(12) United States Patent
Fornell

(10) Patent No.: US 11,497,884 B2
(45) Date of Patent: Nov. 15, 2022

(54) SLEEP AID SYSTEM INCLUDING SMART POWER HUB

(71) Applicant: Happiest Baby, Inc., Los Angeles, CA (US)

(72) Inventor: Peter Fornell, Los Angeles, CA (US)

(73) Assignee: HB Innovations, Inc., Los Angeles, CA (US)

( * ) Notice: Subject to any disclaimer, the term of this patent is extended or adjusted under 35 U.S.C. 154(b) by 273 days.

(21) Appl. No.: 16/431,207

(22) Filed: Jun. 4, 2019

(65) Prior Publication Data

US 2020/0384239 A1    Dec. 10, 2020

(51) Int. Cl.
| | |
|---|---|
| *A61M 21/02* | (2006.01) |
| *H04B 5/00* | (2006.01) |
| *A61M 21/00* | (2006.01) |

(52) U.S. Cl.
CPC ........... *A61M 21/02* (2013.01); *H04B 5/0037* (2013.01); *A61M 2021/005* (2013.01);
(Continued)

(58) Field of Classification Search
CPC ...... A61M 2021/0022; A61M 2230/63; A61M 2205/505; A61M 21/02;
(Continued)

(56) References Cited

U.S. PATENT DOCUMENTS

| | | |
|---|---|---|
| 1,332,400 A | 3/1920 | Johnson |
| 1,897,258 A | 2/1933 | Jenne |

(Continued)

FOREIGN PATENT DOCUMENTS

| | | |
|---|---|---|
| CA | 2459037 | 8/2005 |
| CA | 2760609 | 11/2010 |

(Continued)

OTHER PUBLICATIONS

Emfit, "Instructions for Use, Emfit Tonic-Clonic Seizure Monitor," User manual; online; Jul. 2, 2014 (retrieved May 28, 2020); www.safetysystemsdistribution.co.uk/content/Emfit%20Manuals/Emfit%20Tonix-Clonic%20Seizure%'20Monitor%20User%20Guide.pdf, p. 19 (Year: 2014).*

(Continued)

*Primary Examiner* — Christine H Matthews
*Assistant Examiner* — Joshua Daryl D Lannu
(74) *Attorney, Agent, or Firm* — Akerman LLP

(57) ABSTRACT

A smart power hub for a sleep aid device includes a data communication system for transmitting and receiving data between the sleep aid device and a user communication device and/or network. The data communication system may include a network module for providing wireless data communication access to the user communication device and/or network with respect to the sleep aid device. The smart power hub may be in data communication with the sleep aid device via a wired connection. The wired connection may include a cable having length greater than two meters. The smart power hub may also include a power system for transmitting power to the sleep aid device. The cable may also couple the power system to the sleep aid device for delivering a supply of power to the sleep aid device.

16 Claims, 15 Drawing Sheets

(52) U.S. Cl.
CPC ............... *A61M 2021/0022* (2013.01); *A61M 2021/0027* (2013.01); *A61M 2205/3584* (2013.01); *A61M 2205/3592* (2013.01); *A61M 2240/00* (2013.01)

(58) Field of Classification Search
CPC ...... A61M 2021/0027; A61M 2230/50; A61M 2021/005; A61M 2230/42; A61M 2205/3584; A61M 2205/8206; A61M 2205/3592; A61M 2240/00; H04B 5/0037
See application file for complete search history.

(56) References Cited

U.S. PATENT DOCUMENTS

| | | |
|---|---|---|
| D90,696 S | 9/1933 | Caldwell |
| D128,488 S | 7/1941 | Buckner |
| D158,030 S | 4/1950 | Wagner |
| 2,508,110 A | 5/1950 | Hansen |
| 2,523,422 A | 9/1950 | Dunn |
| 2,808,828 A | 10/1957 | Rubin |
| 2,873,458 A | 2/1959 | Adamson |
| 2,974,325 A | 3/1961 | Mango |
| 2,992,440 A | 7/1961 | Revolt |
| 3,146,736 A | 9/1964 | Hetrick |
| 3,536,067 A | 10/1970 | Sternagel |
| D224,822 S | 9/1972 | Lee, Jr. |
| 3,789,439 A | 2/1974 | Berg |
| D232,279 S | 8/1974 | White |
| 3,886,607 A | 6/1975 | Dunn |
| D244,890 S | 7/1977 | Adams |
| 4,553,485 A | 11/1985 | Lee |
| 4,611,353 A | 9/1986 | Als et al. |
| 4,619,270 A | 10/1986 | Margolis |
| 4,750,223 A | 6/1988 | D'Arcy |
| 4,934,997 A | 6/1990 | Skakas |
| D316,339 S | 4/1991 | Taylor |
| 5,037,375 A | 8/1991 | Gatts |
| D320,316 S | 10/1991 | Arnold |
| 5,129,406 A | 7/1992 | Magnuson et al. |
| 5,183,457 A | 2/1993 | Gatts et al. |
| 5,228,155 A | 7/1993 | Shultz |
| 5,295,490 A | 3/1994 | Dodakian |
| 5,385,153 A | 1/1995 | Jamieson et al. |
| 5,398,353 A | 3/1995 | Sachathamakul |
| D367,979 S | 3/1996 | Lewis |
| 5,577,450 A | 11/1996 | Huang |
| 5,640,717 A | 6/1997 | Ray |
| 5,668,780 A | 9/1997 | Hsieh |
| 5,684,460 A | 11/1997 | Scanlon |
| 5,706,533 A | 1/1998 | Opheim |
| 5,711,045 A | 1/1998 | Caster et al. |
| 5,806,113 A | 9/1998 | McMahan et al. |
| D401,454 S | 11/1998 | De Blaay |
| 5,845,350 A | 12/1998 | Beemllier et al. |
| 5,852,827 A | 12/1998 | Lear et al. |
| 5,855,031 A | 1/1999 | Swift |
| 5,881,408 A | 3/1999 | Bashista et al. |
| D413,454 S | 9/1999 | Kasem |
| D417,090 S | 11/1999 | Reynolds |
| D418,440 S | 1/2000 | Dallaire |
| 6,009,576 A | 1/2000 | Gramme et al. |
| 6,011,477 A | 1/2000 | Teodorescu et al. |
| 6,146,332 A | 11/2000 | Pinsonneault |
| 6,148,455 A | 11/2000 | Kasem |
| 6,155,976 A | 12/2000 | Sackner et al. |
| 6,386,986 B1 | 5/2002 | Sonner |
| 6,393,612 B1 | 5/2002 | Thach et al. |
| 6,415,442 B1 | 7/2002 | Smith et al. |
| 6,498,652 B1 | 12/2002 | Varshneya et al. |
| 6,588,033 B1 | 7/2003 | Welsh, Jr. |
| 6,594,834 B2 | 7/2003 | Fenty |
| 6,652,469 B2 | 11/2003 | Pinsonnault |
| 6,662,390 B1 | 12/2003 | Berger et al. |
| 6,839,924 B2 | 1/2005 | Sims et al. |
| 6,868,566 B2 | 3/2005 | Gatten et al. |
| 6,907,626 B1 | 6/2005 | Welsh |
| 6,916,249 B2 | 7/2005 | Meade |
| 6,928,674 B2 | 8/2005 | Blackburn |
| 6,966,082 B2 | 11/2005 | Bloemer et al. |
| D512,466 S | 12/2005 | White |
| 6,978,479 B2 | 12/2005 | Thach et al. |
| D518,942 S | 4/2006 | Dandrea |
| 7,043,783 B2 | 5/2006 | Gatten et al. |
| 7,076,819 B2 | 7/2006 | Trani et al. |
| D526,133 S | 8/2006 | Song |
| 7,100,724 B2 | 9/2006 | Haigh et al. |
| 7,123,758 B2 | 10/2006 | Mostafavi et al. |
| D536,191 S | 2/2007 | Kasem |
| D536,550 S | 2/2007 | Kasem |
| 7,181,789 B2 | 2/2007 | Gatten et al. |
| 7,203,981 B1 | 4/2007 | Cowgill et al. |
| 7,246,392 B2 | 7/2007 | Schmid et al. |
| D561,978 S | 2/2008 | Soulides |
| 7,337,482 B2 | 3/2008 | Byrne et al. |
| 7,347,806 B2 | 3/2008 | Nakano et al. |
| 7,406,725 B2 | 8/2008 | Martin et al. |
| 7,427,921 B2 | 9/2008 | Van |
| 7,485,086 B2 | 2/2009 | Dickie et al. |
| 7,587,769 B1 | 9/2009 | McDermott et al. |
| 7,587,772 B2 | 9/2009 | Ward et al. |
| D605,870 S | 12/2009 | Bergkvist |
| D606,282 S | 12/2009 | Chen |
| 7,685,657 B1 | 3/2010 | Hernandez et al. |
| D613,091 S | 4/2010 | Taylor |
| 7,722,118 B2 | 5/2010 | Bapst et al. |
| D616,665 S | 6/2010 | Dumais |
| 7,743,442 B2 | 6/2010 | Maloney et al. |
| 7,774,875 B1 | 8/2010 | Zeidman et al. |
| 7,785,257 B2 | 8/2010 | Mack et al. |
| 7,857,677 B2 | 12/2010 | Kamm |
| 7,918,505 B2 | 4/2011 | King et al. |
| D640,483 S | 6/2011 | Daley et al. |
| 7,954,187 B1 | 6/2011 | Earnest et al. |
| D644,413 S | 9/2011 | Keall |
| 8,011,037 B1 | 9/2011 | Earnest et al. |
| 8,032,958 B2 | 10/2011 | Pieta et al. |
| D650,153 S | 12/2011 | Chopak et al. |
| 8,083,601 B2 | 12/2011 | Speedie et al. |
| 8,096,960 B2 | 1/2012 | Loree et al. |
| 8,112,835 B2 | 2/2012 | Elrich et al. |
| 8,141,186 B2 | 3/2012 | Jackson et al. |
| 8,191,188 B2 | 6/2012 | Kaplan et al. |
| 8,197,005 B2 | 6/2012 | Hopke et al. |
| 8,239,984 B2 | 8/2012 | Hopke et al. |
| 8,269,625 B2 | 9/2012 | Hoy et al. |
| D669,659 S | 10/2012 | Barski |
| 8,302,225 B1 | 11/2012 | Earnest et al. |
| 8,321,980 B2 | 12/2012 | Maloney et al. |
| D674,614 S | 1/2013 | Morand |
| 8,347,432 B2 | 1/2013 | Schmid et al. |
| 8,365,325 B2 | 2/2013 | Schneider et al. |
| 8,375,486 B2 | 2/2013 | Earnest et al. |
| D678,693 S | 3/2013 | Bergkvist |
| 8,395,510 B1 | 3/2013 | Kirk |
| 8,398,538 B2 | 3/2013 | Dothie et al. |
| 8,429,771 B2 | 4/2013 | Long et al. |
| 8,522,375 B2 | 9/2013 | Conrad et al. |
| 8,539,620 B1 | 9/2013 | Wynh et al. |
| D692,209 S | 10/2013 | Dragu |
| 8,555,414 B2 | 10/2013 | Davis et al. |
| 8,561,227 B2 | 10/2013 | Jenkins et al. |
| D696,486 S | 12/2013 | Barski |
| 8,607,364 B2 | 12/2013 | Barski et al. |
| 8,607,366 B2 | 12/2013 | Austin |
| 8,661,582 B2 | 3/2014 | Sclare et al. |
| 8,667,631 B2 | 3/2014 | Coates et al. |
| 8,695,133 B2 | 4/2014 | Christensen et al. |
| 8,726,437 B2 | 5/2014 | Hardesty et al. |
| 8,745,794 B1 | 6/2014 | McDermott |
| 8,756,731 B1 | 6/2014 | Huttner et al. |
| 8,769,737 B1 | 7/2014 | Duggins et al. |
| 8,776,265 B2 | 7/2014 | Neveu et al. |
| 8,777,311 B1 | 7/2014 | Laurel et al. |

(56) References Cited

U.S. PATENT DOCUMENTS

| | | |
|---|---|---|
| 8,782,831 B2 | 7/2014 | Houston et al. |
| 8,784,227 B2 | 7/2014 | Speedie et al. |
| D715,027 S | 9/2014 | Haut et al. |
| 8,827,366 B2 | 9/2014 | Daley et al. |
| 8,832,880 B2 | 9/2014 | Sheard et al. |
| 8,845,440 B2 | 9/2014 | Hayt et al. |
| 8,863,329 B2 | 10/2014 | Sofia-Mcintire et al. |
| D718,017 S | 11/2014 | Barski |
| 8,898,833 B2 | 12/2014 | Coates et al. |
| 8,904,580 B1 | 12/2014 | Christensen et al. |
| 8,910,332 B2 | 12/2014 | Buckson |
| 8,942,783 B2 | 1/2015 | Cervantes et al. |
| 8,943,625 B2 | 2/2015 | Gotel et al. |
| 9,003,564 B2 | 4/2015 | Wynh |
| 9,020,622 B2 | 4/2015 | Shoham et al. |
| D728,198 S | 5/2015 | Barski |
| D728,199 S | 5/2015 | Barski |
| 9,032,963 B2 | 5/2015 | Grissom |
| 9,069,549 B2 | 6/2015 | Buckson |
| D734,592 S | 7/2015 | Castillo et al. |
| 9,119,423 B2 | 9/2015 | Gotel et al. |
| 9,131,734 B2 | 9/2015 | Daugherty et al. |
| D741,046 S | 10/2015 | Pelekanou |
| 9,155,403 B2 | 10/2015 | Mountz et al. |
| D742,097 S | 11/2015 | Dunn |
| 9,179,711 B2 | 11/2015 | Krawchuk |
| D751,847 S | 3/2016 | Brown |
| 9,392,881 B1 | 7/2016 | Schmelzle |
| D780,472 S | 3/2017 | Behar |
| 9,962,012 B1 | 5/2018 | Schmid et al. |
| D825,219 S | 8/2018 | Karp et al. |
| 10,265,013 B2 * | 4/2019 | Lim ................ A61B 5/6823 |
| 2002/0016991 A1 | 2/2002 | Brown |
| 2002/0100116 A1 | 8/2002 | Richards et al. |
| 2004/0070254 A1 | 4/2004 | Conlon et al. |
| 2004/0078895 A1 | 4/2004 | Eiling et al. |
| 2005/0022284 A1 | 2/2005 | Thach |
| 2005/0091743 A1 | 5/2005 | Bioemer et al. |
| 2005/0120459 A1 | 6/2005 | McConnell et al. |
| 2005/0210592 A1 | 9/2005 | Littlehorn et al. |
| 2005/0283908 A1 | 12/2005 | Wong et al. |
| 2006/0025226 A1 | 2/2006 | Nakano et al. |
| 2006/0042013 A1 | 3/2006 | Madsen |
| 2006/0084514 A1 | 4/2006 | Speedie et al. |
| 2006/0096031 A1 | 5/2006 | Foster |
| 2006/0225206 A1 | 10/2006 | Kasem |
| 2007/0056109 A1 | 3/2007 | Forshpan et al. |
| 2007/0060015 A1 | 3/2007 | Glatt et al. |
| 2007/0061968 A1 | 3/2007 | Fader |
| 2007/0085695 A1 | 4/2007 | Nerurkar et al. |
| 2007/0267904 A1 | 11/2007 | Clapper et al. |
| 2008/0077020 A1 | 3/2008 | Young et al. |
| 2008/0136236 A1 | 6/2008 | Kincaid et al. |
| 2008/0196164 A1 | 8/2008 | Calilung |
| 2008/0217150 A1 | 9/2008 | Chen |
| 2008/0314665 A1 | 12/2008 | Sanders et al. |
| 2009/0062622 A1 | 3/2009 | Lin et al. |
| 2009/0064390 A1 | 3/2009 | Beiring et al. |
| 2009/0131185 A1 | 5/2009 | Speedie |
| 2010/0044164 A1 | 2/2010 | Thome |
| 2010/0201171 A1 | 8/2010 | Velderman et al. |
| 2010/0218299 A1 | 9/2010 | Damir |
| 2010/0225489 A1 * | 9/2010 | Hinterlong ............ A61B 5/103 340/573.4 |
| 2010/0228315 A1 | 9/2010 | Nielsen |
| 2010/0231421 A1 | 9/2010 | Rawls-Meehan |
| 2010/0253504 A1 | 10/2010 | Lliteras et al. |
| 2010/0257654 A1 | 10/2010 | Waters et al. |
| 2010/0275373 A1 | 11/2010 | Kaplan |
| 2010/0298742 A1 | 11/2010 | Perlman |
| 2010/0328075 A1 | 12/2010 | Rahamim et al. |
| 2011/0025915 A1 | 2/2011 | Daban et al. |
| 2011/0032103 A1 | 2/2011 | Bhat et al. |
| 2011/0078855 A1 | 4/2011 | Buckson et al. |
| 2011/0099719 A1 | 5/2011 | Hardesty et al. |
| 2011/0116549 A1 | 5/2011 | Riddiford et al. |
| 2011/0179546 A1 | 7/2011 | Millette et al. |
| 2011/0277210 A1 | 11/2011 | Hardesty et al. |
| 2011/0308011 A1 | 12/2011 | Cheng |
| 2012/0025992 A1 | 2/2012 | Tallent et al. |
| 2012/0083670 A1 | 4/2012 | Rotondo |
| 2012/0125347 A1 | 5/2012 | Soileau et al. |
| 2012/0216349 A1 | 8/2012 | Kaplan et al. |
| 2012/0297518 A1 | 11/2012 | Aiken et al. |
| 2012/0311762 A1 | 12/2012 | Aiken et al. |
| 2013/0123654 A1 | 5/2013 | Rahamim et al. |
| 2013/0139290 A1 | 6/2013 | Barski et al. |
| 2013/0165809 A1 | 6/2013 | Abir |
| 2013/0185867 A1 | 7/2013 | Long et al. |
| 2014/0059762 A1 | 3/2014 | Bonczek |
| 2014/0068834 A1 | 3/2014 | Skinner |
| 2014/0130254 A1 | 5/2014 | Jeong |
| 2014/0173822 A1 | 6/2014 | Doering et al. |
| 2014/0249382 A1 | 9/2014 | Bhat et al. |
| 2014/0250558 A1 | 9/2014 | Russo |
| 2014/0250592 A1 | 9/2014 | Karp et al. |
| 2014/0265480 A1 | 9/2014 | Perrin et al. |
| 2014/0339867 A1 | 11/2014 | Daley et al. |
| 2014/0345042 A1 | 11/2014 | Morand |
| 2015/0026886 A1 | 1/2015 | Gangan |
| 2015/0045608 A1 | 2/2015 | Karp et al. |
| 2015/0059089 A1 | 3/2015 | Falkiner |
| 2015/0126819 A1 | 5/2015 | Cervantes |
| 2015/0250330 A1 | 9/2015 | Mountz et al. |
| 2015/0250419 A1 | 9/2015 | Cooper et al. |
| 2016/0128392 A1 | 5/2016 | Krawchuk |
| 2016/0165961 A1 | 6/2016 | Karp |
| 2016/0166081 A1 | 6/2016 | Karp et al. |
| 2016/0174619 A1 | 6/2016 | Waters |
| 2016/0174728 A1 | 6/2016 | Karp et al. |
| 2016/0310067 A1 | 10/2016 | Heinrich et al. |
| 2017/0043117 A1 | 2/2017 | Karp et al. |
| 2017/0043118 A1 | 2/2017 | Karp et al. |
| 2018/0035082 A1 * | 2/2018 | Patil ........................ G06T 7/246 |
| 2019/0088102 A1 * | 3/2019 | Furuland ............ G08B 21/0211 |

FOREIGN PATENT DOCUMENTS

| | | | |
|---|---|---|---|
| CA | 2848529 | 3/2013 | |
| CA | 2918029 | 4/2016 | |
| CN | 1701732 A | 11/2005 | |
| CN | 201042329 A | 4/2008 | |
| CN | 101756556 A | 6/2010 | |
| CN | 201664114 U | 12/2010 | |
| CN | 102727004 A | 10/2012 | |
| DE | 102013210164 | 12/2014 | |
| DE | 102013210164 A1 * | 12/2014 | ............ G08C 17/02 |
| EP | 0617907 | 6/1997 | |
| EP | 1435810 | 7/2004 | |
| EP | 1748711 | 2/2007 | |
| EP | 2617329 | 7/2013 | |
| EP | 2197322 | 2/2014 | |
| EP | 2292124 | 7/2014 | |
| EP | 2768345 | 8/2014 | |
| EP | 2915459 | 9/2015 | |
| EP | 292812 | 10/2015 | |
| EP | 2756136 | 8/2016 | |
| FR | 2669201 | 5/1992 | |
| GB | 2312374 | 10/1997 | |
| JP | 07275091 | 10/1995 | |
| JP | 07289394 | 11/1995 | |
| JP | 2000510022 | 8/2000 | |
| KR | 1020040097883 | 11/2004 | |
| KR | 20060019024 A | 3/2006 | |
| KR | 1020060079587 | 7/2006 | |
| KR | 20090121797 A | 11/2009 | |
| KR | 101740285 | 5/2017 | |
| KR | 101740285 B1 * | 5/2017 | |
| WO | 199817150 A2 | 4/1998 | |
| WO | 2004107927 A1 | 12/2004 | |
| WO | 2007062499 | 6/2007 | |
| WO | 2010098702 | 9/2010 | |
| WO | 2013038248 | 3/2013 | |
| WO | 2013059625 | 4/2013 | |

(56) References Cited

FOREIGN PATENT DOCUMENTS

| | | | | |
|---|---|---|---|---|
| WO | 2013087955 | 6/2013 | | |
| WO | 2013135975 | 9/2013 | | |
| WO | 2013188810 | 12/2013 | | |
| WO | 2014078442 | 5/2014 | | |
| WO | 2015017709 | 2/2015 | | |
| WO | 2015143430 | 9/2015 | | |
| WO | 2015157440 | 10/2015 | | |
| WO | WO-2015157440 A1 * | 10/2015 | ........... | H04N 5/2256 |
| WO | 2016055946 | 4/2016 | | |
| WO | 2016096518 | 6/2016 | | |
| WO | 2016123619 | 8/2016 | | |
| WO | 2016138441 | 9/2016 | | |

OTHER PUBLICATIONS

Edge Banding, Kreg Newsletter, Nov. 2014, site visited Jun. 15, 2017, available online <URL:http://www.popularwoodworking.com/projects/iron-on-edge-banding>.

Iron-on Edge Banding, Popular Woodworking Magazine, Sep. 19, 2008, site visited Jun. 15, 2017, available online <URL:http://www.popularwoodworking.com/projects/iron-on-edge-banding>.

Oval Crib, Fine Woodworking, http://www.finewoodworking.com/readerproject/2009/11/11/oval-crib, Nov. 11, 2009.

SNOO Bassinet, Can this High-Tech Bassinet Keep Sleep-Deprived Parents Sane?, The Wall Street Journal, http://www.wsj.com/articles/can-this-high-tech-bassinet-keep-sleep-deprived-parents-sane, Oct. 18, 2018.

Office Action issued in Australian Application No. 2012325947, dated Aug. 22, 2016.

Office Action issued in Mexican Patent Application No. MX/a/2014/004648, dated Mar. 24, 2017.

Extended European search report issued in European Patent Application No. 14831425.5, dated Feb. 24, 2017.

Putting Baby in SNOO Sack, https://www.youtube.com/watch?v=NvTIOzWxG80, Oct. 28, 2016.

About SUID and SIDS, Centers for Disease Control and Prevention, http://www.cdc.gov/sids/ aboutsuidandsids.htm, Oct. 3, 2016, (accessed Nov. 3, 2016), 2 pages.

Infant Sleep Forum Posting, http://www.sleepnet.com/ infant/messages/501.html, (accessed Mar. 16, 2015), 2 pages.

Safety Standard for Bassinets and Cradles; Correction, Federal Register, vol. 78, No. 247, https://www.bderalregistergov/documents/2013/12/24/2013-30527/safety-standard-for-bassinets-and-cradles-correction (accessed Nov. 10, 2016), Consumer Product Safety Commission, Dec. 24, 2013, 1 page.

Safety Standard for Bassinets and Cradles; Correction, Federal Register, vol. 78, No. 205, https://www.bderalregistergov/documents/2013/10/23/2013-24203/safety-standard-for-bassinets-and-cradles (accessed Nov. 10, 2016), Consumer Product Safely Commission, Oct. 23, 2013, 18 pages.

Safety Standard for Bedside Sleepers, Federal Register, vol. 79, No. 10, https://www.federalregister.gov/documents/2014/01/15/2014-00597/safety-standard-for-bedside-sleepers, (accessed Nov. 10, 2016), Consumer Product Safety Commission, Jan. 15, 2014, 9 pages.

SIDS and Other Sleep-Related Infant Deaths: Expansion of Recommendations for a Safe Infant Sleeping Environment, Task Force on Sudden Infant Death Syndrome, Pediatrics, vol. 128, No. 5, Nov. 2011, pp. e1341, 29 pages.

EP Application No. 12781007.5, Examination Notification Art. 94(3) dated May 5, 2015, Unacuna, LLC, 3 Pages.

AAP Task Force on SIDS, The Changing Concept of Sudden Infant Death Syndrome: Diagnostic Coding Shifts, Controversies Regarding the Sleeping Environment, and New Variables to Consider in Reducing Risk, Peds, vol. 116, 2005, pp. 1245-1255.

Ariagno, et al., Fewer spontaneous arousals during prone sleep in preterm infants at 1 and 3 months corrected age, Journal of Perinatology, vol. 26, 2006, pp. 306-312.

Carpenter, et al., Sudden unexplained infant death in 20 regions in Europe: case control study, The Lancet, vol. 363, No. 9404, 2004, pp. 185-191.

Colvin, et al., Sleep Environment Risks for Younger and Older Infants, Pediatrics, vol. 134, Jul. 2014, pp. e406-e412.

Galland, et al., Prone versus supine sleep position: a review of the physiological studies in SIDS research, J Paediatr Child Health, vol. 38, No. 4, Aug. 2002, pp. 332-338.

Groswasser, et al., Reduced arousals following obstructive apneas in infants sleeping prone, Pediatric Research, vol. 49, No. 3, 2001, pp. 402-406.

Horne, et al., Effects of body position on sleep and arousal characteristics in infants, Early Human Development, vol. 69, iss. 1-2, Oct. 2002, pp. 25-33.

Horne, et al., The prone sleeping position impairs arousability in term infants, The Journal of Pediatrics, vol. 138, No. 6, 2001, pp. 811-816.

Kato, et al., Spontaneous Arousability in Prone and Supine Position in Healthy Infants, Sleep, vol. 29, No. 6, 2006, pp. 785-790.

L'Hoir, et al., Risk and preventive factors for cot death in The Netherlands, a low-incidence country, Eur J Pediatr, fol. 157, 1998, pp. 681-688.

Li et al., Infant Sleeping Position and the Risk of Sudden Infant Death Syndrome in California, 1997-2000, Am J Epidemiol, vol. 157, No. 5, 2003, pp. 446-455.

McDonnell, et al., Infant Deaths and Injuries Associated with Wearable Blankets, Swaddle Wraps, and Swaddling, J. Pediatr., vol. 164, No. 5, May 2014, pp. 1152-1156.

Mitchell, et al., Changing Infants' Sleep Position Increases Risk of Sudden Infant Death Syndrome, Arch Ped Adol Med., vol. 153, 1999, pp. 1136-1141.

Oyen, et al., Combined effects of sleeping position and prenatal risk factors in sudden infant death syndrome: the Nordic Epidemiological SIDS Study, Pediatrics, vol. 100, No. 4, 1997, pp. 613-621.

International Preliminary Report On Patentability With Written Opinion for PCT/US2012/061069, dated May 1, 2014.

International Search Report and Written Opinion for PCT/US2012/061069, dated Mar. 11, 2012.

International Preliminary Reporton Patentability for PCT/US2014/049253, dated Feb. 11, 2016.

Internationai Search Report and Written Opinion for PCT/US2014/049253, dated Nov. 24, 2014.

International Search Report and Written Opinion for PCT/US2016/019878, dated May 6, 2016.

Pease, et al., Swaddling and the Risk of Sudden Infant Death Syndrome: A Meta-analysis, Pediatrics, vol. 137, No. 3, Jun. 2016, pp. e20153275 (11 pages).

Ponsonby, et al., Factors potentiating the risk of Sudden Infant Death Syndrome associated with the Prone Position, NEJM, vol. 329, 1993, pp. 377-382.

Shapiro-Mendoza, et al., Trends in Infant Bedding Use: National Infant Sleep Position Study, 1993-2010, Pediatrics, vol. 135, 2015, pp. 10-17.

Tuladhar, et al., Effects of sleep position, sleep state and age on heart rate responses following provoked arousal n term infants, Early human development, vol. 71, iss. 2, Apr. 2003, pp. 157-169.

Vennemann, et al., Sleep Environment Risk Factors for Sudden Infant Death Syndrome: The German Sudden Infant Death Syndrome Study, Pediatrics, vol. 123, No. 4, Apr. 2009, pp. 1162-1170.

International Search Report and Written Opinion for PCT/US2019/019010, dated May 24, 2019.

Naver blog; URL:https:/blog.naver.com/redtony02/30103163614.

Notification of International Search Report and Written Opinion, PCT/US2020/027084, dated Jun. 22, 2020.

Emfit, "Instructions for Use, Emfit Tonic-Clonic Seizure Monitor," User manual; online; Jul. 2, 2014 (retrieved May 28, 2020); www.safetysystemsdistribution.co.uk/content/Emfit%20Manuals/Emfit%20Tonix-Clonic%20Seizure%20Monitor%20User%20Guide.pdf, p. 19.

* cited by examiner

SLEEP AID SYSTEM INCLUDING SMART POWER HUB

TECHNOLOGY FIELD

The present disclosure relates to sleep aid systems including sleep aid devices. More specifically, the present disclosure relates to providing power and data communication capabilities, such as wireless access, for sleep aid devices.

BACKGROUND

Attempts have been made to engineer technological methods to create improved powered sleep aid devices that deliver motion to a platform onto which an infant is positioned and/or sound to the infant. Such devices may be used to calm or soothe the infant. Some such devices incorporate sensors for detecting motions or sounds of the infant. However, data communication with sleep aid devices and peripherals is lacking. Thus, there is a need to improve communication systems with respect to sleep aid devices.

SUMMARY

In one aspect, a smart power hub for a sleep aid device includes a power module for transmitting power to the sleep aid device and a data communication system for transmitting and receiving data between the sleep aid device and a user communication device or network.

In various embodiments, the data communication system may include a network module configured to provide wireless access for data communications between the sleep aid device and the user communication device or network.

The smart power hub may be configured to transmit and receive data communications to and from the sleep aid device via a wired connection and transmit and receive data communications to the user communication device or network via wireless communication utilizing the network module. The network module may be configured for communication within a wireless personal area network protocol to provide a user device wireless communication with the network module via the personal area network to control operations of the sleep aid device. In one example, the wireless personal area network protocol may be carried over Bluetooth wireless network technology. In a further example, the Bluetooth wireless network technology is Bluetooth Low Energy wireless network technology.

In one embodiment, the network module is configured for communication with the user device or network utilizing WiFi technology. In some implementations, the smart power hub supports transmission of continuous 1080p video, continuous streaming audio, or both. In one configuration, the smart power hub is configured to transmit and receive data communications to and from the sleep aid device via a wired connection and transmit and receive data communications to the user communication device or network via wireless communication utilizing the network module. In an example, the wired connection may comprises a cable having a length of at least 2 meters. The cable may transmit both power from the power module and data communications from the data communication system.

In various embodiments, the smart power hub provides an internet access point and is configured to receive software updates via internet communications to update the smart power hub. The smart power hub may provide an internet access point and be configured to receive software updates via internet communications to update the sleep aid device. The smart power hub may provide an internet access point to the user device. The smart power hub may provide an internet access point to a user device running an application configured to communicate with the sleep aid device. In one example, the smart power hub provides an internet access point to a user device running an application configured to communicate with the sleep aid device when the user device is authenticated. In a further example, the application is configured to provide control and communication functions with respect to the sleep aid device.

In some embodiments, the network module is configured with wireless networking capabilities using both WiFi and Bluetooth technologies. The network module may provide Bluetooth/Bluetooth Low Energy technology support for in-application authentication, wherein the application is configured to provide control and communication functions with respect to the sleep aid device. In some examples, the network module provides Bluetooth/Bluetooth Low Energy technology support for WiFi configuration, WiFi configuration including passing credentials, support for controlling a Bluetooth Low Energy technology peripheral, in-application authentication, or combination thereof.

In one embodiment, the smart power hub is configured to transmit power and data communications to the sleep aid device using a single cable. In one embodiment, the smart power hub comprises data communication and power functions in a form factor of a power supply, which can be coupled directly to the wall outlet via prongs or use an intermediate cable. The power module may be operable to convert alternating current to direct current.

In another aspect, a sleep aid system includes a sleep aid device comprising a platform, a motor to move the platform, one or more sensors for monitoring an infant when positioned on the platform, and a control system operable to control operation of the motor to thereby control a movement of the platform. The control system may be configured to receive infant data collected by the one or more sensors with respect to the infant when positioned on the platform. The control system may be configured to modify the movement of the platform based on analysis of the infant data. The sleep aid system may comprise a smart power hub, such as a smart power hub as described above with respect to the previous aspect or elsewhere herein.

In still another aspect, a smart power hub for wireless communication with an electronic device configured to operate in proximity of an infant or child includes a data communication system for transmitting and receiving data between the electronic device and a user communication device or network. The data communication system may include a network module configured to provide wireless access for data communications between the electronic device and the user communication device or network. The smart power hub may transmit and receive data communications to and from the electronic device via a wired connection and transmit and receive data communications to the user communication device or network via wireless communication utilizing the network module.

The network module may be configured for communication within a wireless personal area network protocol to provide a user device in wireless communication with the network module via the personal area network to control operations of the electronic device. The wireless personal area network protocol may be carried over Bluetooth wireless network technology. The Bluetooth wireless network technology may be Bluetooth Low Energy wireless network technology. Additionally or alternatively, the network module may be configured for communication with the user device or network utilizing WiFi technology.

The smart power hub may support transmission of continuous 1080p video or continuous streaming audio. The smart power hub may support transmission of continuous 1080p video and continuous streaming audio.

The smart power hub may transmit and receive data communications to and from the electronic device via a wired connection and transmit and receive data communications to the user communication device or network via wireless communication utilizing the network module. The wired connection may comprise a cable. In one example, the cable has a length of at least 2 meters.

The smart power hub may further include a power module to provide power to the electronic device. The cable may transmit both power from the power module and data communications from the data communication system. In one embodiment, a separate cable may be used to transmit all or a portion of the power.

The smart power hub may provide an internet access point and be configured to receive software updates via internet communications to update the smart power hub. The smart power hub may provide an internet access point and be configured to receive software updates via internet communications to update the electronic device. In one example, the smart power hub may provides an internet access point to the user device. The smart power hub may provide an internet access point to a user device running an application configured to communicate with the electronic device. The smart power hub may provide an internet access point to a user device running an application configured to communicate with the electronic device when the user device is authenticated. The application may provide control and communication functions with respect to the sleep aid device.

The network module may be configured with wireless networking capabilities using both WiFi and Bluetooth technologies. The network module may provide Bluetooth/Bluetooth Low Energy technology support for in-application authentication, wherein the application is configured to provide control and communication functions with respect to the electronic device. The network module may provide Bluetooth/Bluetooth Low Energy technology support for in-application authentication. The application may be configured to provide control and communication functions with respect to the sleep aid device. The network module may provide Bluetooth/Bluetooth Low Energy technology support for in-application authentication, WiFi configuration, which may include passing credentials, for controlling a Bluetooth Low Energy technology peripheral, or combination thereof.

The smart power hub may be configured to transmit power and data communications to the sleep aid device using a single cable. The smart power hub may comprises data communication and power functions in a form factor of a traditional power supply configured to couple directly to a wall outlet, or via an intermediate cable. The power module may be operable to convert alternating current to direct current.

In yet still another aspect, a system for spacing wireless transmission signals from an electronic device includes an electronic device configured to be positioned proximate to an infant or child during a data communication operation and a smart power hub, such as the smart hub described above with respect to the previous aspect or elsewhere herein.

BRIEF DESCRIPTION OF THE DRAWINGS

The novel features of the described embodiments are set forth with particularity in the appended claims. The described embodiments, however, both as to organization and manner of operation, may be best understood by reference to the following description, taken in conjunction with the accompanying drawings in which:

DESCRIPTION

Figure 1:
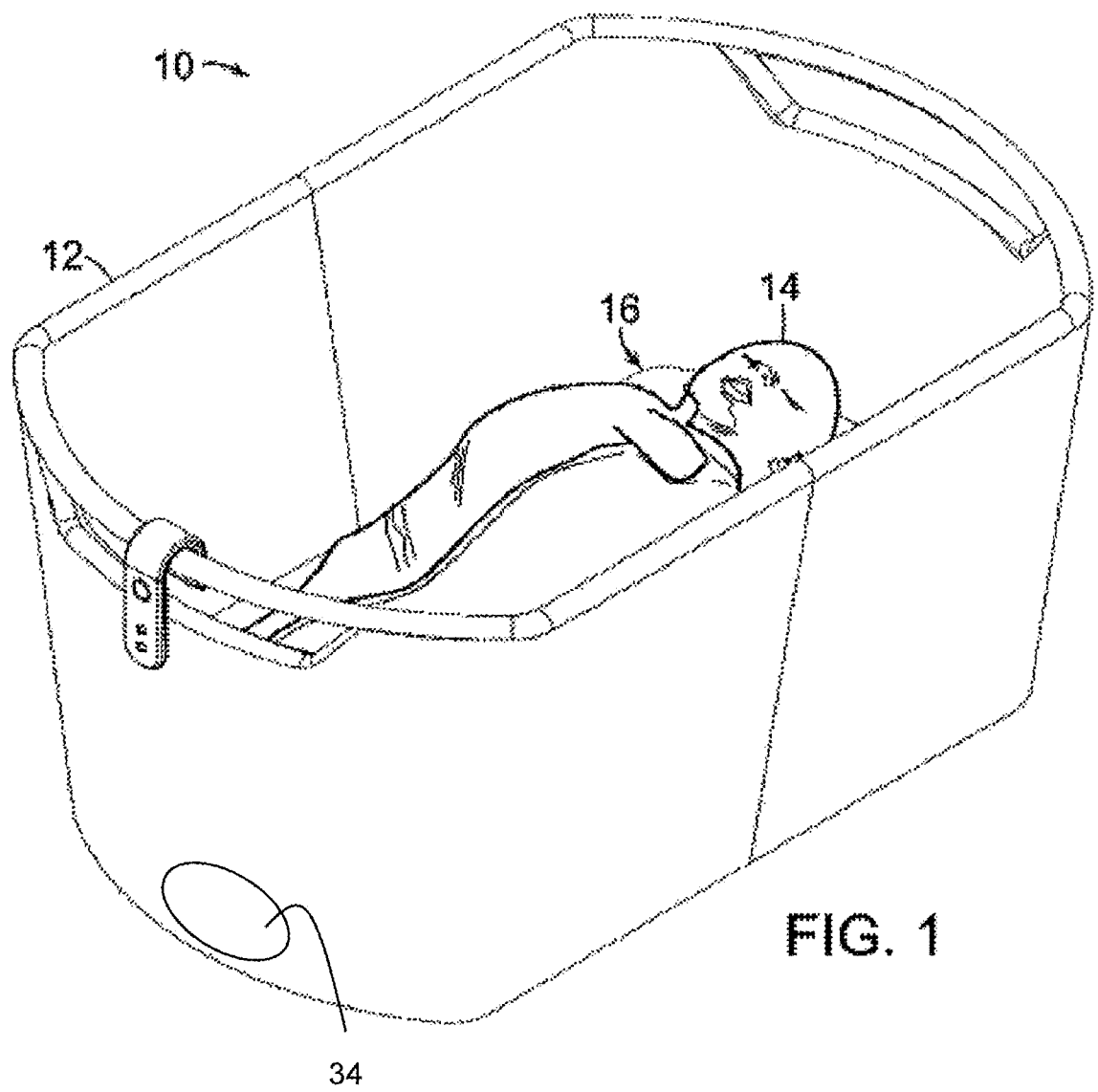
FIG. 1 illustrates a sleep aid device according to various embodiments described herein.

The present disclosure describes a sleep aid system including a smart power hub. The smart power hub may be configured to provide a data communication access point with respect to a sleep aid device, which may be part of the sleep aid system or may operatively associate with the sleep aid system. In various embodiments, the sleep aid device may include a bassinet for an infant, which may include an infant calming/sleep-aid device as described in U.S. patent application Ser. No. 15/055,077, filed Feb. 26, 2016, titled Infant Calming/Sleep-Aid and SIDS Prevention Device with Drive System, or U.S. patent application Ser. No. 15/336,519, filed Oct. 27, 2016, titled Infant Calm/Sleep-Aid, SIDS Prevention Device, and Method of Use. The disclosures of both of which are hereby incorporated by reference herein.

A sleep aid device may include a smart infant sleeper configured to calm babies in minutes and train them to be better sleepers in days by invoking a calming reflex. In various embodiments, the sleep aid device may be configured to automatically generate motion and sound in response to baby cry to illicit a calming response. The motion and sound may escalate until baby is calmed and then may diminish in intensity. If crying persists beyond an intended cycle (e.g., the persistence is indicative of the baby being hungry or ill), the sleep aid device may stop motion of the platform and alert a caregiver. In some embodiments, however, the smart power hub may be configured for operation with a sleep aid device that does not move to illicit a calming response, does not emit sound to illicit a calming response, or both.

Data communication with the sleep aid device may allow a user to interact with the sleep aid device and/or sleep aid device peripherals. For example, a user, utilizing a communication link between a user interface, which may be a remote user interface, and the sleep aid device may receive infant data, device status data, or media data, for example, or transmit updates, media data, controls operations, or data requests, for example. The communication link may be wired or wireless. For example, a smart power hub may provide a wireless access point to the sleep aid device and may be connected to the sleep aid device via a wired data communication link. Utilizing the data communication link, the sleep aid device may be provided with software updates and/or peripherals may be expanded, updated, or controlled. In one implementation, smart power hub may provide a wireless, e.g., WiFi technology, connection that may be used to transfer device status with respect to the sleep aid device. In further examples, the connection may be used to support media content such as continuous transmission of video, e.g., 1080p video, and streaming audio. A local, ad hoc, or personal network connection may also be utilized for media support content or to provide secured access or configuration settings. In one such example, Bluetooth/BLE technology support may be used for in-app authentication, WiFi technology configuration, e.g., including passing credentials. Further applications may include control of motion, sound, or other operations of the sleep aid device from a user device or interface, e.g., from a BLE connected peripheral device. Adding wireless technology, or other high-speed data communication technologies, in close proximity to an infant may leave some parents concerned and to not prefer using the additional benefits of a connected device. However, placing network interfaces, such as wireless, in the power supply that is physically separate from the device, help alleviate such concerns due to the distance from the communication function to the infant.

According to various embodiments, the smart power hub provides power and wireless functions (e.g., WiFi and BLE) to the sleep aid device in the form factor of a power supply. The smart power hub may provide desirable wireless communication functions while having wireless transmitters movable away from an infant within the sleep aid device. The smart power hub may include a single cable for power and data transmission. The above and other features of a sleep aid system including a smart power hub according to various embodiments described herein are described below with reference to the drawings.

FIG. 1 illustrates an example of a sleep aid device 10. The sleep aid device 10 may be configured for infant calming in addition to instead of aiding in sleep. The sleep aid device 10 may be configured for SIDS prevention as described in U.S. patent application Ser. No. 15/055,077, filed Feb. 26, 2016, titled Infant Calming/Sleep-Aid and SIDS Prevention Device with Drive System, or U.S. patent application Ser. No. 15/336,519, filed Oct. 27, 2016, titled Infant Calm/Sleep-Aid, SIDS Prevention Device, and Method of Use. The sleep aid device 10 includes an enclosure 12 about an infant 14. The enclosure 12 surrounds a platform 16.

Figure 2:
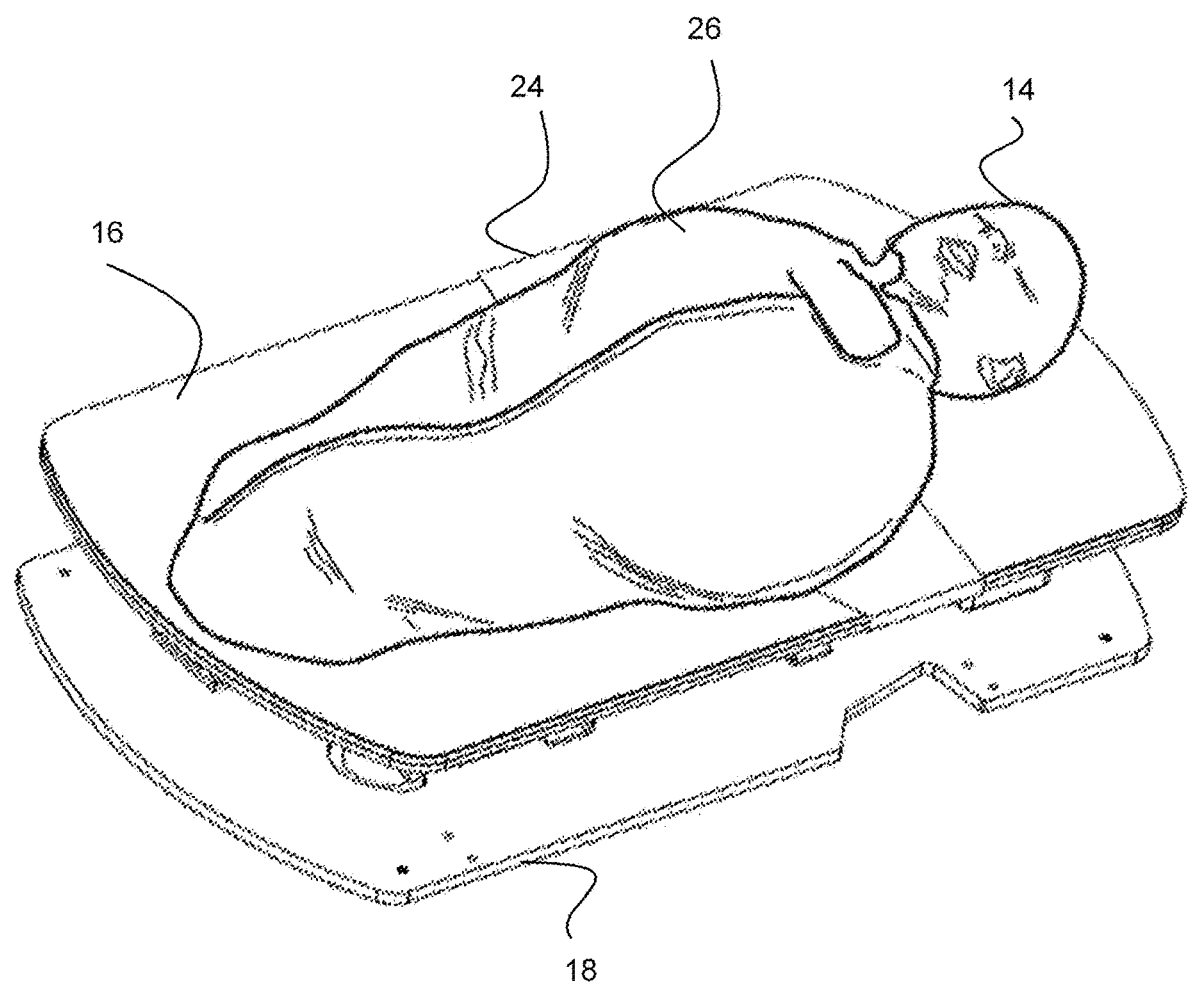
FIG. 2 illustrates a movable platform of a sleep aid device according to various embodiments described herein.

In an embodiment, with reference to FIG. 2, the platform 16 may be configured to move relative to a base 18, such as in a manner as described in U.S. patent application Ser. No. 15/055,077, filed Feb. 26, 2016, titled Infant Calming/Sleep-Aid and SIDS Prevention Device with Drive System, or U.S. patent application Ser. No. 15/336,519, filed Oct. 27, 2016, titled Infant Calm/Sleep-Aid, SIDS Prevention Device, and Method of Use. In some embodiments, the platform 16 may move in a reciprocating motion. For example, the platform 16 may rock back-and-forth or may rotate side-to-side about an axis that is orthogonal to a major plane of platform 16. In various embodiments, the sleep aid device 10 may be equipped with one or more safety features to prevent a baby from rolling onto their stomach, prevent a baby from falling out of device, prevent overexposure to loud nose, reduce risk of overheating, and/or prevent hip dysplasia. In some embodiments, the sleep aid device may include a sleep sack for swaddling a baby. The infant 14 may be swaddled in a sleep sack 26 that may be secured to the platform 18 with sack fastening straps 24 that extend from the sleep sac 26 for secure attachment of the sleep sack 26 to the platform 16. In one embodiment, the sleep sack fastening straps 24 may comprise attachment clips and may be integral to the sleep sack 26. The sleep sack 26 attachment mechanism may be configured to attach to the platform 16 such that the infant 14 is secured to the platform on its back. In this manner, the sleep aid device may prevent infants from rolling to the stomach, which is a cause of Sudden Infant Death Syndrome (SIDS) and suffocation-related deaths.

With reference again to FIG. 1, the sleep aid device 10 may include a control panel 34 for interfacing with operations of the sleep aid device 10. For example, the control panel 34 may include buttons, speed control knobs, status lights, power wiring or power plugs for delivery of power to the sleep aid device 10, data wiring or data ports, which may include wired or wireless communication ports, for receiving data, transmitting data, or both. The sleep aid device 10 may further include drive electronics as well as sensors, such as a motion sensor, sound sensor, biometric sensors or other sensors (not shown). In one embodiment, the sleep aid device 10 further includes a microphone (not shown). It will be appreciated that the control panel 34 may be located at other locations with respect to the sleep aid device 10, including multiple locations.

The sleep aid device 10 may further include a control system configured to control the operations of the sleep aid device 10. The interface with the control panel 34 as described elsewhere herein. The control system may include an electronic processor and an electronic data storage medium storing instructions executable by the processor to control the operations of the sleep aid device 10. The control system may operatively couple to the control panel 34 and drive electronics.

In one embodiment, the control system includes or is configured to receive data from a biometric sensor configured to monitor the infant 14 and generate a signal indicative of a respiration status or a cardiovascular status of the infant, such as to detect when the baby has paused breathing for a predetermined period of time, or has a cardiovascular collapse, such as indicated by a heart rate below a predetermined threshold, or the like. The sensor signal can be fed back through control electronics or/and control panel 34 to the control system, which may include software, either on-board or remote from sleep aid device 10. The control system may receive and analyze the signal to determine whether a distressed status of the infant exists, and further may act, such as to generate an output to control modulation of the drive electronics to modulate a drive motor, amplitude modulation motor, generate a telephone call to emergency services via a data connection, and/or generate alerting and stimulating sounds that may be emitted from speakers. In another or a further embodiment, an alarm may be directed at caretakers.

In some embodiments, in response to detection of infant distress, both vigorous motion of the platform 16 and a loud sound from a speaker can be provided. For example, providing motion of the platform 16 at a frequency greater than 0.5 Hz and an amplitude that is greater than 1 inch, along with sound having an intensity of at least 65 dB, may provide appropriate stimulation of the infant. Of course, other amounts of stimulation are also envisioned.

Figure 3:
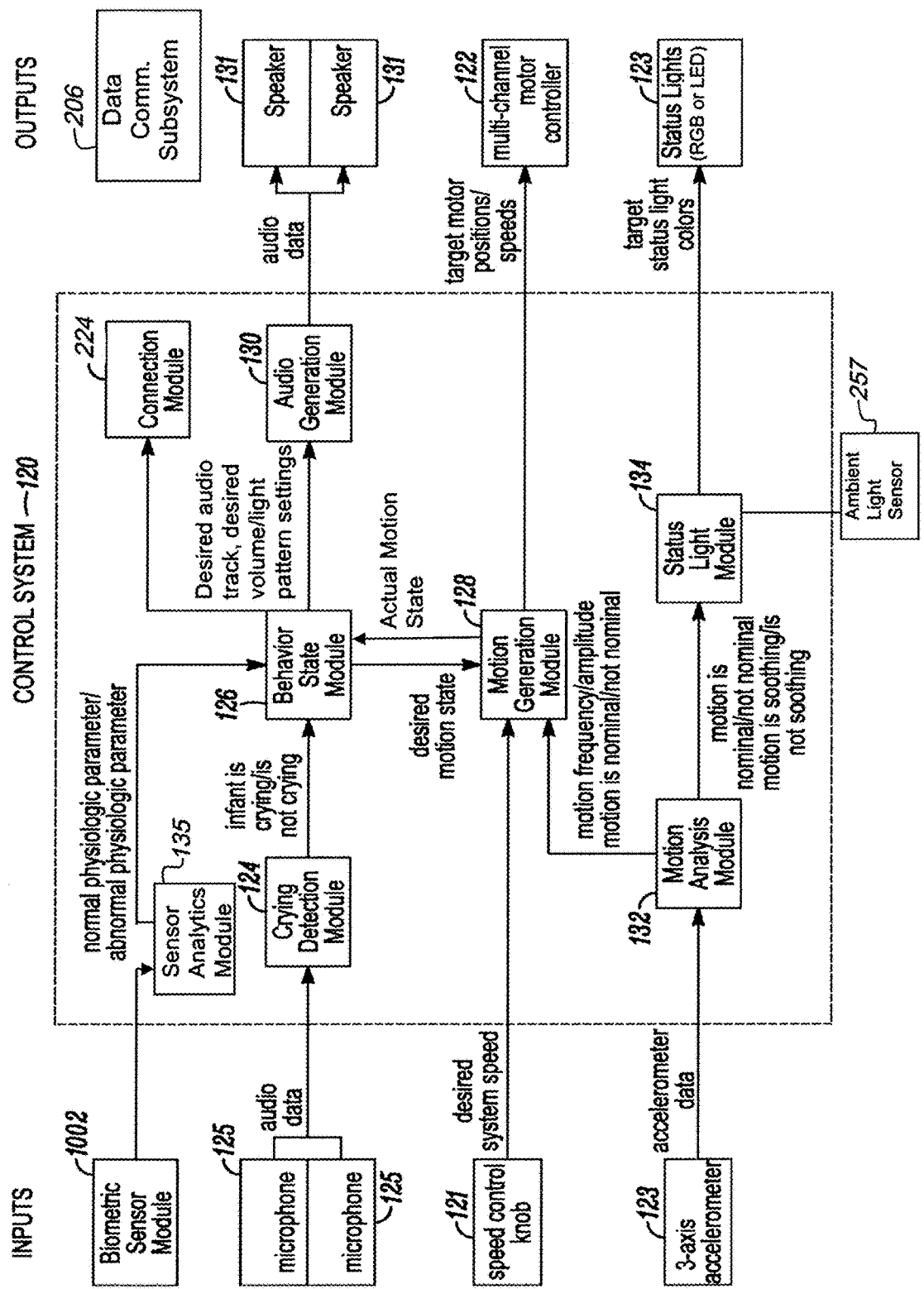
FIG. 3 schematically illustrates various operations of a control system for a sleep aid device according to various embodiments described herein.

FIG. 3 illustrates features of a control system 120 for a sleep aid device according to various embodiments. The control system 120 may receive various inputs from a variety of sensors or control input devices representing desired settings or the like and, based on one or more of these inputs, acts to control one or more of various devices, such as to control sound, motion, and/or lights of the sleep aid device, or to initiate an emergency call or alarm. In the illustrated example, the control system 120 is configured to processes inputs from a multitude of microphones 125, from speed control knob 121, and from a three-axis accelerometer 123, and from a biometric sensor 1002, such as a wireless sensor for detecting one or more of cardiac and respiratory status. Control system 120 may generate one or more output signals, such as to control speakers 131, and to multichannel motor controller 122, which controls one or more motors such as a drive motor, amplitude modulation motor, as examples. Status lights, such as tricolor LEDs 121 can also be controlled. Logic or control modules of control system 120 can be located on-board or remotely from the sleep aid device. The modules may include a crying detection module 124 that receives data from microphones 125, and relays to a behavior state machine module 126 whether or not an infant on sleep aid device is crying or not crying. Microphones 125 may be mounted on the sleep aid device, integrated into the sleep aid device, included in a sensor that is placed on or attached to the infant, and the like. Biometric sensor module 1002 may relay one or more of an infant's physiologic parameters (e.g., breathing status, temperature, motion status, etc.) to the behavior state module 126, or depending on the signal provided by the sensor, directly to a connection Module 224. Depending upon the input received by behavior state machine module 126, output signals will control motion generation module 128 or audio generation module 130 or a Wi-Fi phone connection module 1004. Alternatively, or in addition, output signals from behavior state machine module 126 will modulate generation of audio data output from audio generation module 130 to speakers 131.

Motion generation module 128 receives input from speed control knob 121 and information regarding motion of the device from motion analysis module 132. Actuation of speed control knob 121 may modulate drive motor that drives motion of the platform.

Data received from accelerometer 123 may be processed by motion analysis module 132 to thereby modulate the drive motor through motion generation module 128 and/or audio generation module 130 to thereby control the movement of the platform or speakers, respectively. In addition, motion analysis module 132 may control status light module 134 to alert, through the status lights, whether motions of the platform are nominal or not nominal and the actual motion state, or alternatively, through feedback, soothing or not soothing to the infant. "Nominal", as that term is defined herein, refers to any and all motion for which the filtered acceleration signal does not exceed a specified, or predetermined maximum motion threshold for a specific length of time. The process by which the motion analysis module 132 classifies motion as nominal or not nominal is described with respect to FIG. 5 and in the accompanying text below. An ambient light sensor 257 may provide data regarding current ambient light from which motion or light settings may be modified to account for ambient light.

In one embodiment, the rate of the reciprocating rotation of the platform is controlled to be within a range of between about one and about four and one-half cycles per second (cps) and with an amplitude of the reciprocating motion at a center of a head of the infant of between about 0.2 inches and about 1.3 inches. In another embodiment, the rate of reciprocating motion is within a range of between about 0.5 and about 1.5 cycles per second and an amplitude of the reciprocating rotation at a center of the head of the infant is in a range of between about 0.25 inches and about 2.0 inches. In differing embodiments, this motion may be parallel to, or orthogonal to the platform supporting the infant's body and head.

In embodiments, the control system 120 may operate in a manner wherein the intensity of maximum stimulation is increased over the course of the first weeks and subsequently weans the infant off the device's motion by incorporating the infant age as a variable used in the behavior state module 126. For example, modulation of motion and/or sound may be further controlled by at least one of the weight of the infant, the age of the infant, and the duration of the detected sounds made by the infant.

FIGS. 4-10 illustrate processing and operations of various modules of the control system 120 according to various embodiments.

Figure 4:
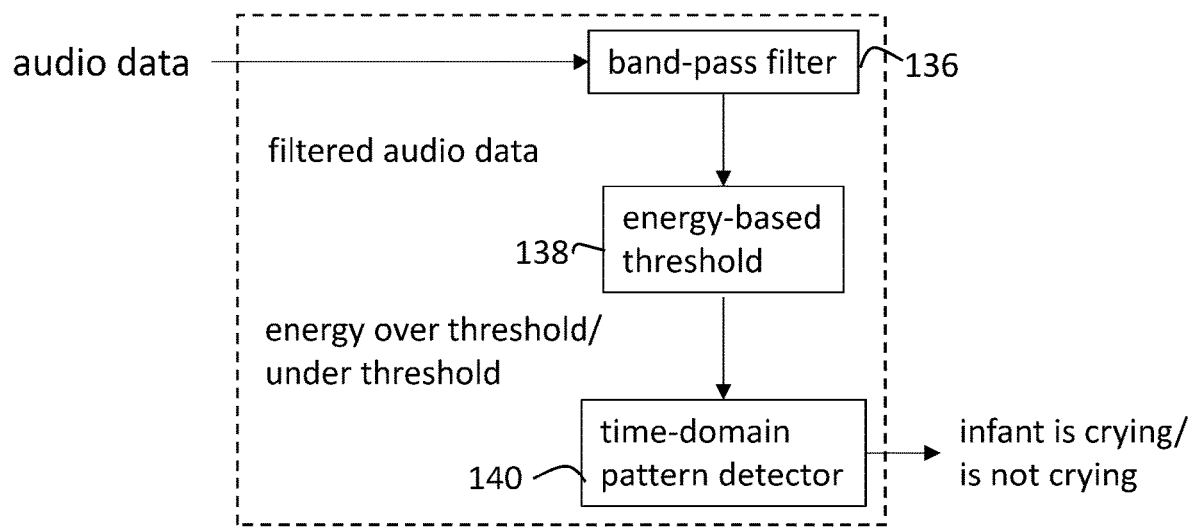
FIG. 4 schematically illustrates various operations of a crying detection module according to various embodiments described herein.

FIG. 4 illustrates operations of a crying detection module 124 according to various embodiments. The crying detection module 124 may receive audio data from the microphones of sleep aid device, which is processed through a band-pass filter 136 to remove undesired signal information. Energy-based threshold 138 receives filtered audio data to determine whether the audio energy is over a preset threshold or under a preset threshold. Time-domain pattern detector 140 receives data from energy-based threshold 138 to provide an indication as to whether the infant is crying or not crying. The information, as discussed above with respect to control system 120 (FIG. 3), is received from crying detection module 124 by behavior state machine module 126 that will then provide signals to control motion generation module 128 or audio generation module 130 or both.

Figure 5:
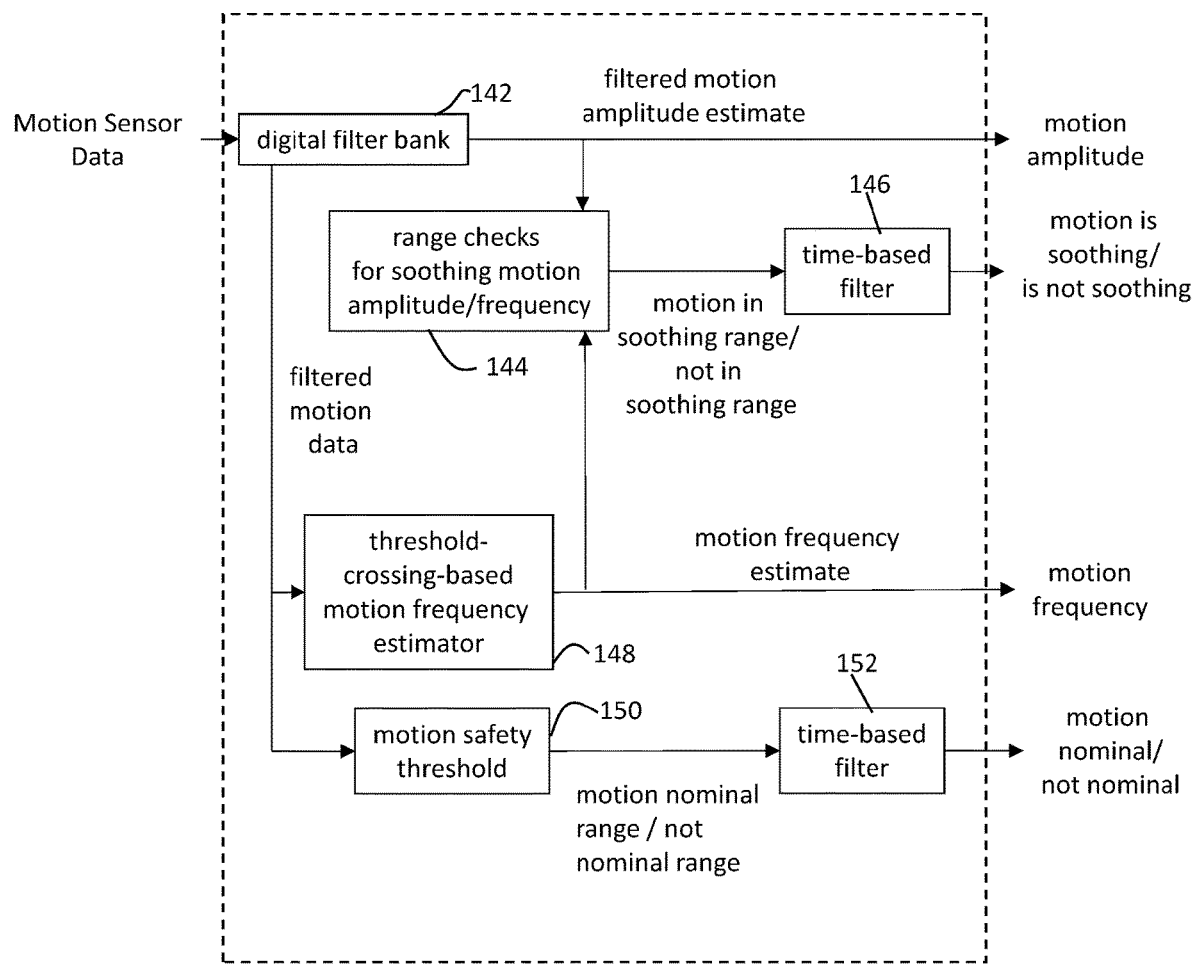
FIG. 5 schematically illustrates various operations of a motion analysis module according to various embodiments described herein.

Motion analysis module 132, shown and represented in more detail in FIG. 5, receives a signal from a motion-sensing device of sleep aid device and applies a digital filter bank 142 to remove undesired signal information. Digital filter bank 142 generates a filtered motion amplitude estimate that is used as input to motion generation module 128 (FIG. 3). In addition, the filtered motion amplitude estimate passes through a range check 144 to determine whether the motion is within a soothing or known soothing range, which is provided to time-based filter 146 and provides an indication as to whether a motion is soothing or not soothing to motion generation module 128 (FIG. 3).

Filtered motion sensor, or accelerometer, data from digital filter bank 142 may also pass through threshold crossing-based motion frequency estimator 148 to provide an estimate of motion frequency, which it provides to motion generation module 128.

Outputted data from threshold-crossing-based motion frequency estimator 148 may also pass through range check 144 for indicating whether the motion is or is not soothing.

Filtered accelerometer data from digital filter bank 142 may also be processed to determine whether or not acceleration exceeds a specific maximum motion threshold 150 and, depending on the result, processes that data through time-based filter 152 to provide an indication as to whether the motion is nominal or not nominal. This indication as to whether the motion is nominal or not nominal is used as input to motion generation module 128 (FIG. 3), and is additionally used to control status lights via status light module 134 (FIG. 3).

Figure 6:
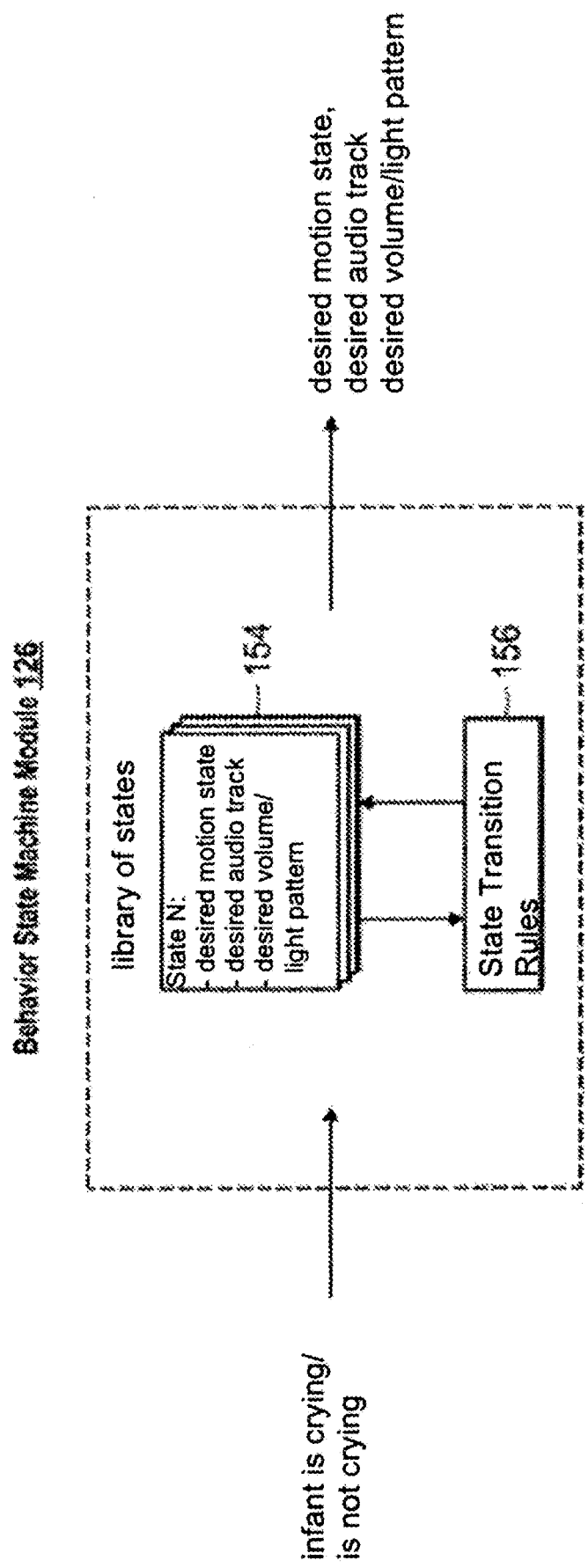
FIG. 6 schematically illustrates various operations of a behavioral state machine module according to various embodiments described herein.

With reference to FIG. 6, behavior state machine module 126 may receive information from crying detection module 124 (FIG. 4) as to whether the infant is in a state of crying or not crying. This information is used by the state machine's state transition rules 156 to select an active state from a library of states 154, thereby outputting a desired motion state, a desired light pattern, a desired audio track and/or desired volume/equalizer settings to audio generation module 130 of FIG. 3.

Figure 7:
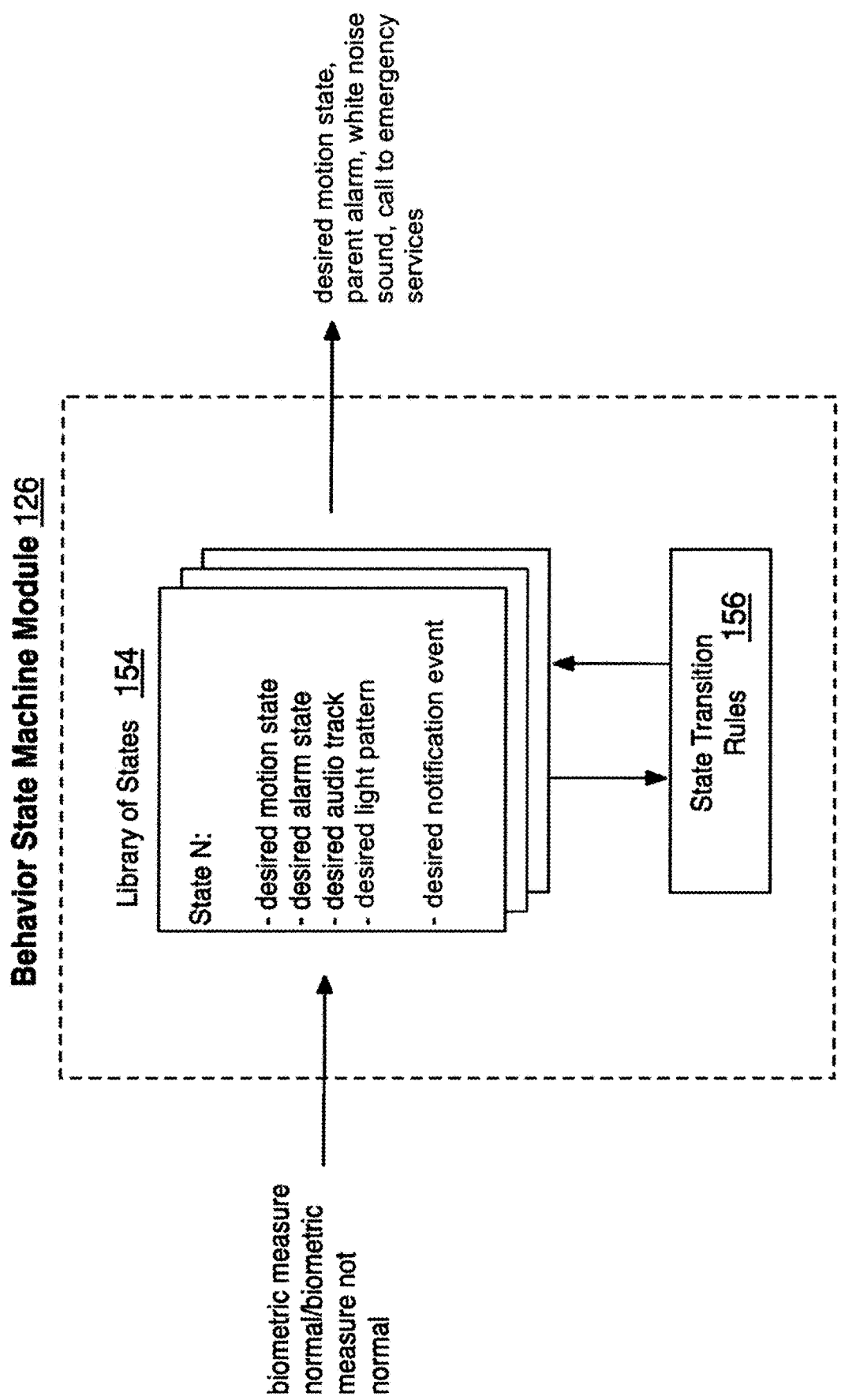
FIG. 7 schematically illustrates various operations of a behavioral state machine module according to various embodiments described herein.

With further reference to FIG. 7, the behavior state machine module 126 may receive information from biometric sensor module 1002 (FIG. 3) as to whether a biometric measure is normal or not normal. One possible biometric measure may be normal if an infant is breathing, not normal if an infant is not breathing, and the like. This information is used by the state machine's state transition rules 156 to select an active state from a library of states 154, thereby outputting a desired motion state, a desired light pattern, a desired audio track and/or desired volume/equalizer settings, a desired notification event that may include a call notification, and the like to audio generation module 130 and the connection module 224 (FIG. 3). One desired motion state, in the case of a not normal signal in such cases as not breathing, is to generate a jolting motion to disrupt the infant state. Desired alarm state may be a parent alarm state and the like. Desired audio track may be a special vigorous white noise track and the like. Desired phone call state may be initiate Wi-Fi phone call to emergency services and the like.

Figure 8:
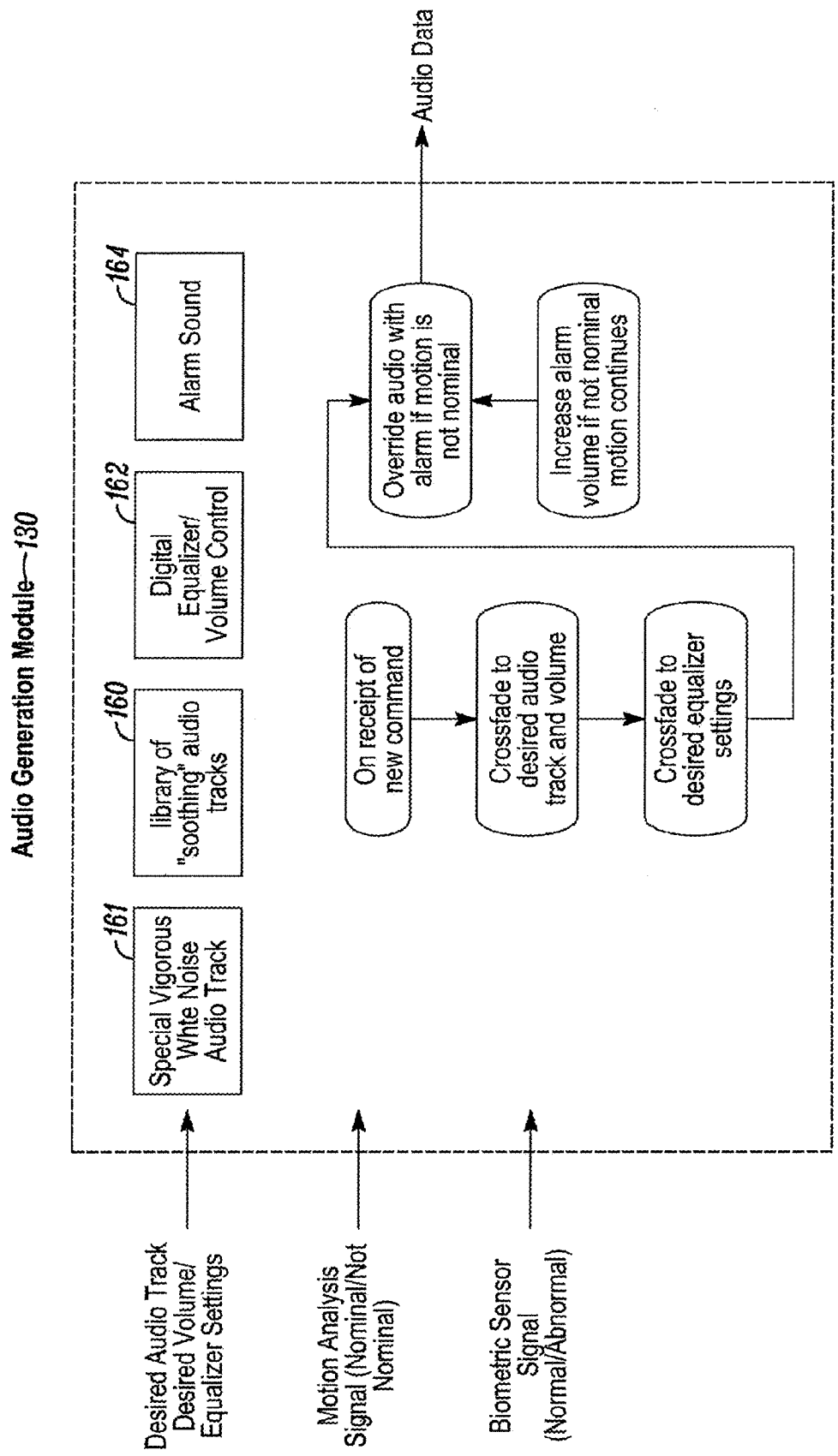
FIG. 8 schematically illustrates various operations of an audio generation module according to various embodiments described herein.

With particular reference to FIG. 8, the audio generation module 130 may be configured to receives signals of a desired audio track and desired volume/equalizer settings from behavior state machine module 126 (FIG. 3) and signals of motion analysis, specifically, whether the motion is nominal or not nominal, from motion analysis module 132 (FIG. 3). Desired audio track may be a sound audio track, music audio track, special vigorous white sound audio track, and the like. Audio generation module 130 includes a special vigorous white noise audio track 161, a library of "soothing" audio tracks 160, a digital equalizer/volume control 162 and alarm sound 164. Upon receipt of a new command from motion analysis module 132 (FIG. 3), audio generation module 130 will cross-fade to a desired audio track and volume, and crossfade to desired equalizer settings. If the motion is not nominal, then an alarm signal may be output to override the audio signal with an alarm. The audio signal from the audio generation module 130 (FIG. 3) is output to the speakers 131 (FIG. 3) of sleep aid device.

At baseline, the audio generator may produce an output of a low-pitch, rumbling sound at about 65 dB to 74 dB. Upon receipt of a new command from crying detection module 124 (FIG. 4), audio generation module 130 may cross-fade to a more high pitched audio track and louder volume, at about 75 dB to 95 dB.

Upon receipt of a new command from behavior state module 126 (FIG. 3), audio generation module 130 will cross-fade to a desired audio track and volume, and cross-fade to desired equalizer settings. If the signal received from the behavior state module 126 is indicative of an abnormal biometric signal that has been detected by the biometric sensor 1002 and sensor analytics module 135 (FIG. 3), for example that an infant is not breathing, then an alarm signal and special vigorous white sound audio track will be output to override the audio signal with an alarm and special vigorous white sound audio track and the Motion Generation Module 128 will output a jolting motion. The special vigorous white sound audio track signal from the audio generation module 130 (FIG. 3) is output to the speakers 131 (FIG. 3) of sleep aid device.

The audio generation module 130 may receive signals from the sensor analytics module 135 (FIG. 3). An abnormal reading, such as a reading indicating that an infant is not breathing, will activate a desired motion pattern and audio track, such as a special vigorous white sound audio track, parent alarm and desired volume/equalizer settings. Upon receipt of a new command from sensor analytics module 135 (FIG. 3), audio generation module 130 will cross-fade to a desired audio track and volume, and crossfade to desired equalizer settings and the motion generation module 128 will output a special jolting motion pattern.

The audio generation module 130 may receive mild signals that indicate an infant is awakening. Mild signals may detect that an infant is mildly awakened. Mild signals may be mild motion signals, mild sound signals, and the like. Mild signals may be sent from a sensor attached to or worn by an infant. Mild signals may be detected from an infant before the infant begins to cry. Audio generation module 130 may begin to increase sound levels when mild signals are received.

Figure 10:
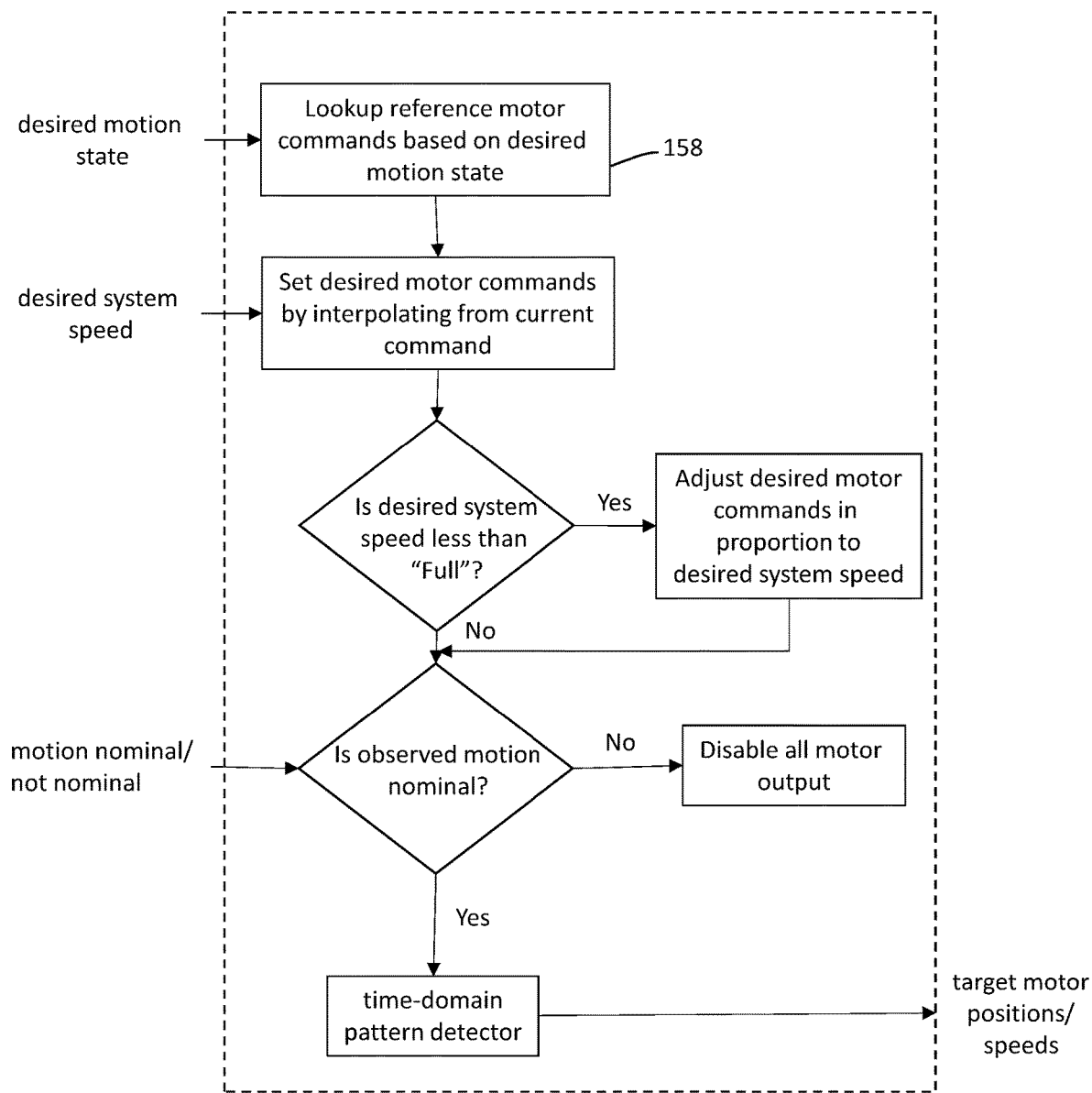
FIG. 10 schematically illustrates various operations of a motion generation module according to various embodiments described herein.

In one embodiment, shown in FIG. 10, the motion generation module 128 may be configured to receive a desired motion state input from behavior state machine module 126 (FIG. 3), a motion frequency/amplitude signal from motion analysis module 132 (FIG. 3), a desired system speed signal from speed control knob 121 (FIG. 3), and a signal as to whether a motion is nominal or is not nominal. The "desired system speed" is the setting of speed control knob 121, whereby the operator can select or limit the motions allowed by sleep aid device. The desired motion state signal performs a lookup within motion generation module 128, which outputs a reference motor command based on a desired motion state. If the currently active motor commands are close to the reference motor commands, then the motor commands are actively adjusted within an allowable envelope via a gradient ascent based on observed motion frequency and amplitude. If the current motor commands are not close to the reference motor commands, then the motion generation module will set desired motor commands via path planning in a motor command space. "Path planning" transitions motor settings to desired motor settings by inserting intermediate motor settings as necessitated by nest dynamics to ensure that motion stays in a desirable range during transition. If the desired system speed is less than "full," then a signal may be sent to adjust the desired motor commands in proportion to the desired system speed. "Full"

is the fully-on position of the knob, and means that sleep aid device is not being limited by this knob and is allowed to perform all of the motions it determines to be relevant. If speed control knob 121 is turned down from "full," motions of sleep aid device start to become constrained, so speed control knob 121 acts as an operator to override the normal motion behavior of sleep aid device. If not, then a comparison is made as to whether the observed motion is nominal. If it is not, then motor output is disabled. If it is nominal, then an output signal of desired motor commands is given to target motor positions and speeds of the actuator of the multichannel motor controller. In some embodiments, sound is delivered to an infant but not motion if an infant is in the device but not securely attached. The level of motion and or sound output may also be modified by the parents' choice of a special boost function.

Figure 9:
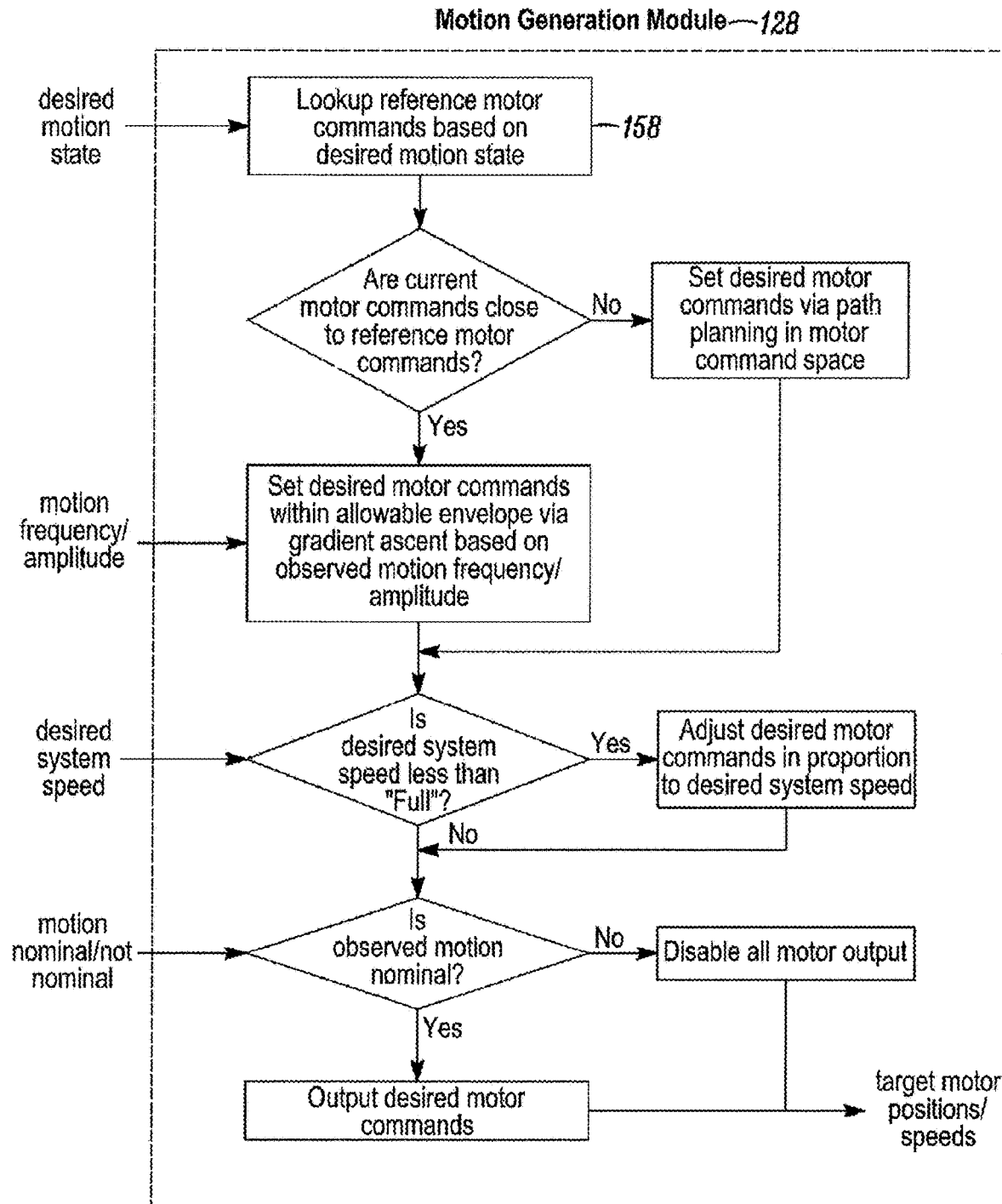
FIG. 9 schematically illustrates various operations of a motion generation module according to various embodiments described herein.

In another embodiment, with reference to FIG. 10, the motion generation module 128 may not receive signals related to motion frequency and amplitude. Therefore, it may only necessary to set desired motor commands by interpolating from a current command based on a look up table of motor commands based on a desired motion state in response to receiving a signal with respect to the desired motion state. All of the other components of motion generation are the same as represented in FIG. 9.

In one embodiment, the motion generation module 128 receives a motion state input of an abnormal signal, for example that an infant is not breathing, from the biometric sensor module 1002 (FIG. 3). The resultant programmed vigorous motion may continue until the abnormal biometric signal is discontinued, for example when an infant begins breathing again, or the device is shut off.

Figure 11A:
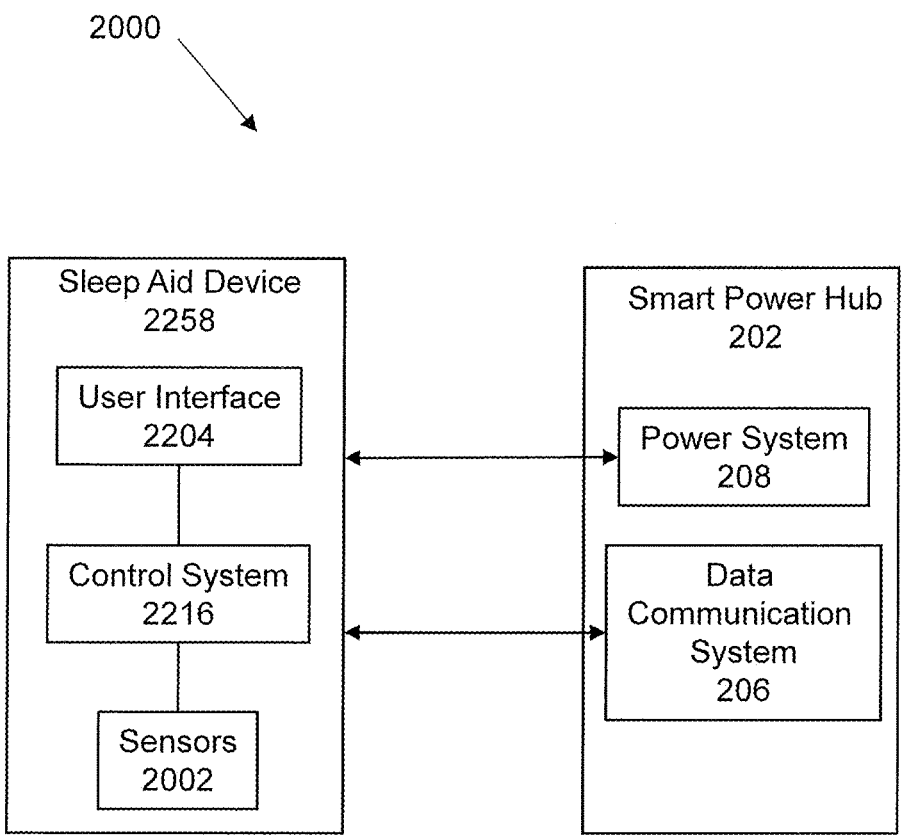
FIG. 11A schematically illustrates a sleep aid system according to various embodiments described herein.

In various embodiments, the control system may be configured to deliver staged interventions of specially engineered sound and motion patterns to the platform. These platform motion patterns may be in a reciprocating manner about an axis that intersects the infant and is orthogonal to a major plane of the surface supporting the infant to provide a motion that varies from slow smooth rocking (0.5-1.5 cps) to keep babies calm and promote sleep; ramp to a faster, smaller, jiggling motion (2-4.5 cps) with a more spiked waveform to deliver a sufficiently abrupt acceleration-deceleration action to stimulate the vestibular mechanism of the inner ear, trigger a calming reflex and soothe the baby, such as when the baby cries (e.g., head rocking back and forth in excursions of less than F) and a special jolting motion designed to wake the infant up from a distressed state. The sound in the device may be adapted to respond to the baby's upset by starting a specially engineered high pitched sound, then stepping down to quieter, lower pitched white noise over several minutes. A wide variety of sound patterns may be enabled. The device may be adapted to gradually increase the intensity of the sound and/or motion during the early weeks of life and to gradually reduce (i.e. wean) the intensity of the sound and/or motion over a suitable time period, such as several weeks or several months later in infancy FIG. 11A is a schematic of a sleep aid system 2000 comprising a sleep aid device 2258 coupled to a smart power hub 2002. The sleep aid device comprises a control system 2216, which may be similar to control system 120 (see, e.g., FIG. 3), a user interface 2204 for interfacing with sleep aid device 2258 or control system 2216 thereof, and one or more sensors 2002.

The user interface 2204 may be provided on the sleep aid device 2204 and may comprise one or more buttons, display screen, touch screen, switches, and/or knobs for interfacing with operations of the sleep aid device 2258 and control system 2216. For example, the user interface 2204 may include a speed control knob to set a desired system speed as described with respect to FIG. 3. While the user interface 2204 is illustrated as associated with the sleep aid device 2204, in various embodiments, the user interface 2204 may connect remotely to the control system 2216 via a wired or wireless connection. As described herein, a remote user interface for communication with the sleep aid device 2204 or control system 2216 may be provided via wired or wireless data connection with data communication system 206. In some embodiments, user interface 2204 includes or may integrate with such a remote interface comprising a user device, which may be a dedicated device, tablet, smart phone, computer, laptop, or other suitable communication device. In some embodiments, a user device may be similar to user device 250 described with respect to FIG. 13.

Sensors 2002 are configured to detect and/or measure states of an infant, motion of a movable platform, sound output from the sleep aid device 2258, environmental or ambient conditions with respect to an infant or the sleep aid device 2258. Sensors may include audio sensors (e.g., microphones), motion sensors (e.g., vibration sensors, video sensors, light or optical sensors, or accelerometers), or other sensors for monitoring states of an infant, movable platform, or environment of the sleep aid device 2258. In some embodiments, the sensors 2002 may include biometric sensors, microphones, ambient light sensors, and/or accelerometers as described with respect to FIGS. 3-10.

Figure 11B:
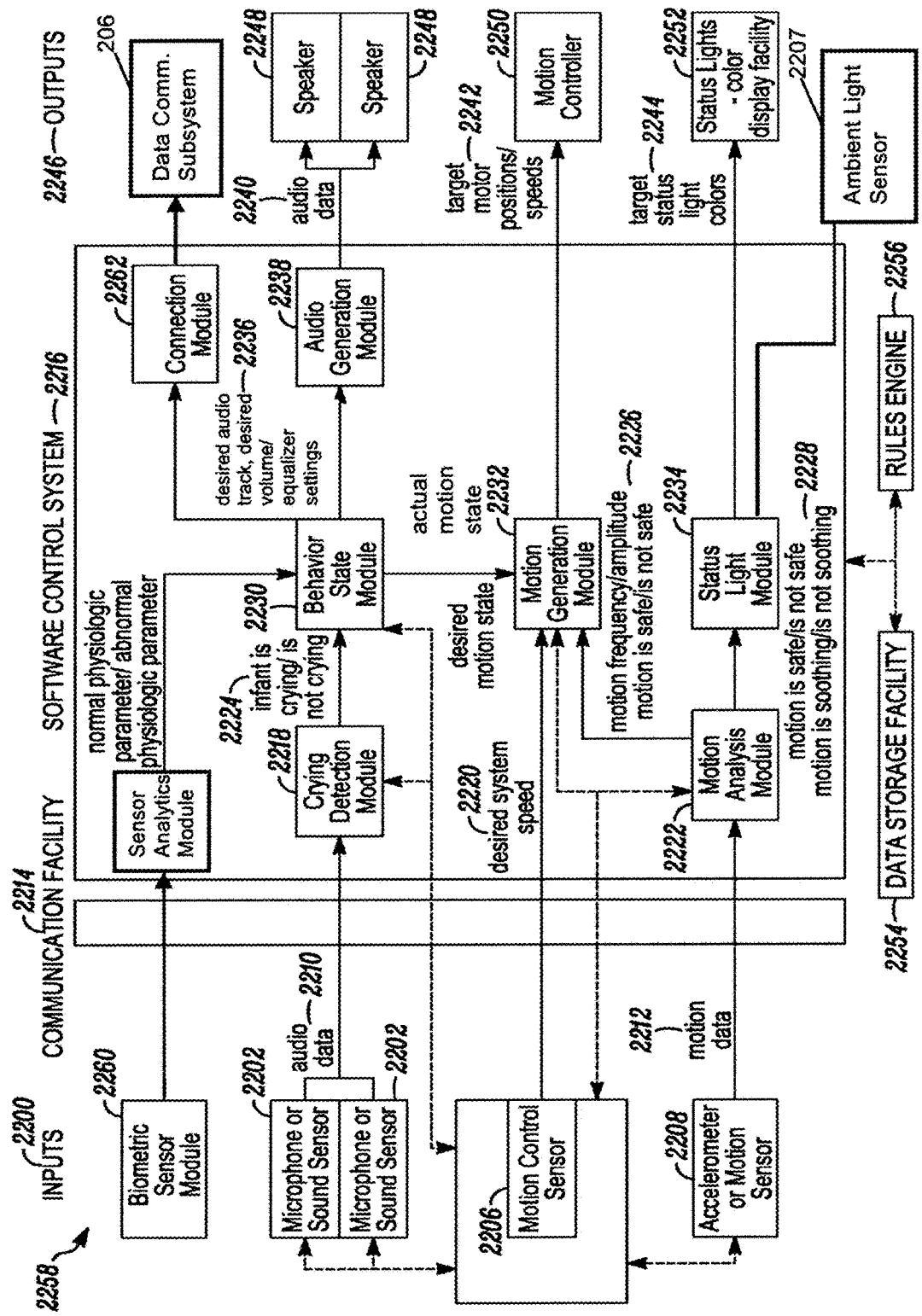
FIG. 11B schematically illustrates various operations of the sleep aid system illustrated in FIG. 11A according to various embodiments described herein.

FIG. 11B illustrates exemplary operations of the sleep aid system 2000 with respect to control system 2216 of the sleep aid device 2258 and including data communication with data communication system 206 of the smart power hub 202 of FIG. 11A, according to various embodiments. The control system 216 may include related components for receiving and processing inputs 2200, which may be provided sensors 2002 as described with respect to FIG. 11A and elsewhere herein, and generating outputs 2246, a user interface 2204 (see FIG. 11A), and a communication facility 2214. Components of the control system 2216 and the user interface 2204 can be located on-board or remotely from an enclosure/platform portion of sleep aid device 2258. Inputs 2200 may include data or control signals from various types of sensors 2002 (FIG. 11A) or devices such as microphone or sound sensor 2202, motion control sensor 2206, accelerometer or motion sensor 2208, user interface 2204, ambient light sensor 2207, biometric sensor 2260, and the like. Outputs from the control system 2216 are directed to devices such as speakers 2248 for controlling the generation of sound, motion controller 2250 for controlling the motion of a platform or structure on which the infant is placed, Wi-Fi phone call to emergency services, and status light facility 2252 for controlling illumination of various status lights, which in some embodiments may incorporate inputs from ambient light sensor 2207.

Other inputs may also be provided by other sensors 2002 (FIG. 11A) such as visual sensors, including cameras, pressure sensors, sensors located in a swaddle or sleep sack, third party sensors, including monitors, sensors embedded in fabrics and the like. Such sensors may be built-in to the sleep aid device 2258, be directly coupled to the sleep aid device 2258 via a wired connection such as USB, via network services or wirelessly via the network module. Sensors 2202 embedded in fabrics may be flexible sensors. Sensors 2202 may be used for detecting child physiological parameters. Sensors 2002 may be used to provide inputs and feedback for mode selection for a mechanism that activates the calming reflex of an infant or, in certain circumstances, increases a baby's arousal. Microphone or sound sensor 2202 may be in communication with user interface 2204. Motion control sensor 2206 may be controlled by user interface 2204. Motion control sensor 2206 may be in communication with motion generation module 2232. Motion control sensor 2206 may send desired system speed input 2220 to motion generation module 2232.

User interface 2204 may be in communication with inputs such as microphone or sound sensors 2202, crying detection module 2218, motion analysis module 2222, accelerometer or motion sensor 2208, and the like. User interface 2204 may allow a user to input data such as the date of birth of an infant, the due date of an infant, the name of the infant, the weight of the infant, and the like. The weight of the infant may be input manually or automatically. The weight of the infant may be input automatically from a scale that is integrated with the sleep aid device 2258. The user interface 2204, or inputs 2200, may be used to provide a diary. The diary may be a sleep diary, cry diary, temperature, feeding and the like. The user interface 2204 may be used to boost baseline stimulation by providing more motion and sound. For example, an extra fast and/or strong sound could be provided for infants that are difficult to calm. This extra fast and/or strong sound could be called Intervention4. Intervention4 may only be able to be activated two consecutive times, until the device is reset. Intervention4 may be limited to about two minutes of operation. The infant calming/sleep aid device may turn off after Intervention4 has been operating for about two minutes.

User interface 2204 may be an integral part of the sleep aid device 2258, or a separate piece, such as on a mobile peripheral device, which may be connected by a wired connection, through local network services, a wireless connection, and the like to the infant calming/sleep aid device 2258, e.g., via the smart power hub 202. The wireless connection may be a Wi-Fi connection, Bluetooth connection, and the like. In one example, the user interface 2204 comprises a user device that wirelessly connects to the control system 2216 via the data communication system 206. In a further example, the user device may execute an application or API providing an interface for interfacing with the control system 2216.

The user interface 2204 may have controls, set-up information input, and other input data that can be sent to the control system 2216 of the device. Controls may include an on/off control, sound control, motion control, light control, and the like. Controls may be enabled or disabled. Motion control may have an extension option that automatically extends the sound, extends the basic motion of the device, and the like. The option that extends the basic motion of the device may be used after an infant is older than four months. Light control may have a dim option, be used to turn and LED alarm light on or off, and the like.

The user interface 2204 may allow a user to input set-up information, other information, and the like. Set-up information may include due date, birthdate, name, nickname, date/time setup, and the like. Other input information may include information related to shots the infant has had, feedings, travel, dirty diapers, and the like.

The user interface 2204 may provide various functions, such as Session, Session 'Super', History, Profile, Settings, Customization, Journaling and the like. Session may include start/stop session, track session duration, track cry and sleep duration, track mode position, session summary, period summary, track epic position, contextual and expert tips messaging, alert messaging, AM/PM model, night light, and the like. Period summary may be for a 12 hour clock or 24 hour clock setup. Session 'Super' may include track mode position, track mode duration, volume control, editable mode position, and the like. History may include compare periods, display AM vs. PM sessions, share data and epic position via email and social, add sleep note to session, add weight note to session, and the like. Compare periods may compare periods over a 12 hour period, a 24 hour period, and the like. Profile may include name/nickname, due date, birth date, and the like. Settings may include overview, getting started, sleep library, level 4 on/off, notifications, push start, milestones, sleep facts, social network setup, sync on/off, and the like. Customization may include editable session data, manual entry, sound on/off, customize sound, customize mode, show weight in profile, allow weight input via external API, light control, and the like. Overview may include content from Epic Education, and the like. Getting Started may include content from First Use Coaching, and the like. Sleep library may include content from eBooks, and the like.

The user interface 2204 may provide cloud based functions. Cloud based functions may include account management, the ability to invite other account holders to manage profile, add friends, compare session data with friends, anonymously post to world data, compare session/period/epic with world data, social commenting, web view of data, and the like.

User interface 2204 may be provided as a mobile application. The mobile application may provide data inputs to the control mechanism of the infant calming/sleep aid device 2258. Data may include monitoring data, feedback data, control data, reporting data, analytics data, and the like. The mobile application may be installed on a mobile device. The device may be a smartphone, tablet computer, and the like. The mobile device may have an operating system that may be iOS, Android, and the like. The mobile application may enable interactions with the device. Interactions may be enabled through a communication interface. The communication interface may be a universal serial bus (USB) interface, Wi-Fi interface, Bluetooth interface, and the like. Interactions may be control interactions. Control interactions may be similar to the interactions that may be enabled directly from the infant calming/sleep aid device 2258, only available on the mobile application, and the like. Examples of control interactions may include the ability to turn on Intervention4 using four fast taps of the on/off button within two seconds, turn on/off the infant calming/sleep aid device 2258 by pressing and holding the on/off button for three seconds, and the like.

Other mobile device interactions may include reports and statistics, sharing and group interactions, benchmarking and comparison interactions, graphic interactions, acoustic signature of a cry interactions, data upload to a third party interactions, feedback from a subject matter expert interactions, warning alert interactions, overtone customization of white noise interactions, other input interactions, journal sharing/printout interactions, weight interactions, breastfeeding interactions, camera interactions, and the like. Other input interactions may include photo input interactions, video input interactions, audio input interactions, and the like.

Additional inputs may include information inputs. Information inputs may include baby weights, baby lengths, baby circumferences, frequencies, travel, immunizations, illness, heart rate, respiratory rate, blood oxygenation, and the like. Baby weights may include weight at birth, baby weights at different weighings, and the like. Baby length may include baby length at birth, baby length at different measurings, and the like. Baby circumference may include baby circumference of the head at birth, baby circumference of the head at different measurings, and the like. Frequencies may include frequency of feeding, frequency of diaper changes/pee or poop, and the like. Information inputs may be added to a mobile device journal.

Microphone or sound sensor 2202 may send audio data 2210 to crying detection module 2218. Accelerometer or motion sensor 2208 may send motion data 2212 to motion analysis module 2222. Communication facility 2214 may be used to establish communication between inputs 2200 and control system 2216. Communication may be established via direct control, remote control, and the like. Direct control may include providing control inputs to the communication facility from input devices directly integrated with the sleep aid device 2258. Remote control may include providing control inputs to the communication facility from input devices remotely connected to the sleep aid device 2258. Remote connectivity may include wired and wireless connectivity. Wireless connectivity may include Wi-Fi connectivity, Bluetooth connectivity, and the like. Journaling may include track feedings, track diapers, and the like.

Control system 2216 may include modules as described above with respect to FIGS. 3-10. Modules may include crying detection module 2218, behavior state module 2230, biometric detection module, audio generation module 2238, motion generation module 2232, motion analysis module 2222, status light module 2234, and the like. Crying detection module may be in communication with microphone or sound sensor 2202, motion control sensor 2206, behavior state module 2230, and the like. Crying detection module 2218 may send an infant crying/not crying status input 2224 to behavior state module 2230. Biometric detection module may be in communication with motion generation module 2232, audio generation module 2238, and the like. Biometric detection module may send desired motion state input 2260 to motion generation module 2232, desired audio track, desired volume/equalizer settings input 2236 to audio generation module 2238, and the like. Behavior state module 2230 may be in communication with crying detection module 2218, motion generation module 2232, audio generation module 2238, and the like. Behavior state module may send desired motion state input 2260 to motion generation module 2232, desired audio track, desired volume/equalizer settings input 2236 to audio generation module 2238, and the like. Motion generation module 2232 may be in communication with behavior state module 2230, motion control sensor 2206, user interface 2204, motion analysis module 2222, motion controller 2250, and the like. Motion analysis module 2222 may be in communication with accelerometer or motion sensor 2203, user interface 2204, motion generation module 2232, status light module 2234, and the like. Motion analysis module 222 may send motion frequency/amplitude and motion is safe/is not safe input 2226 to motion generation module 2232. Motion analysis module 2222 may send motion is safe/not safe input and motion is soothing/is not soothing input 2228 to status light module 2234. Motion generation module may send target motor positions/speeds input to motion controller 2250 and the like. Audio generation module 130 may be in communication with behavior state module 2230 speaker 2248, and the like. Audio generation module 2238 may send audio generation module input to speaker 2248. Status light module 2234 may be in communication with motion analysis module 2222 status lights color display facility 2252 and the like. Status light module 2234 may send target status light colors input 2244 to status lights color display facility 2252 and the like.

Control system 2216 may also be in communication with data storage facility 2254, rules engine 2256, and the like. Data storage facility 2254 may store information that may be accessed by other modules of the control system 2216, and the like. Rules engine 2256 may provide rules for inputs and triggers to a mechanism to activate the "calming reflex" of an infant.

Sleep aid device 2258 may provide a mechanism to activate the calming reflex of an infant, such as via the operation of control system 2216 described with respect to FIGS. 11A & 11B. The mechanism may use stereotypical sensory input, stereotypical behavioral output, and the like to trigger the calming reflex. The activation mechanism may be programmed to wane after 3-5 months or the like. The mechanism may exhibit threshold variations that vary between higher and lower thresholds based on the individual infant. The mechanism may vary by biometric evaluation or state of the infant and may call for higher or lower levels of stimulation based on the state of the infant. The state may be a quiet sleeping state, active sleep state, drowsiness state, quiet alert state, fussing state, crying state, and the like. The state may be matched to the optimal stimulus level of an individual infant. Levels may also be adjusted to match the age of the infant, for example during the first month of the life of the infant. Failure to exceed the optimal stimulus level may result in an absence of response by the infant to the mechanism. The mechanism may be activated by sound generated by the infant, movement generated by the infant, abnormal biometric signals, and the like. The output of the mechanism may cause reductions in motor output levels. The infant calming/sleep aid device 2258 may automatically shut down if an infant is not calmed by higher levels of motion and sound. Higher levels of motion and sound may be called Intervention3 and Intervention4. The infant calming/sleep aid device may teach infants to sleep better by training the sleep pattern of the infant using sleep cues. Sleep cues may be swaddling, effective motion, optimal sound, and the like. Motion may take on characteristics of a more square-shaped wave as the platform moves more quickly.

Activation of the calming reflex or the conditioned response of an infant may be activated by a feedback based control mechanism. The feedback based control mechanism may select modes, parameters, parameter ranges, and the like. Modes may be motion modes, sound modes, and the like. Parameters may be motion parameters, sound parameters and the like. Parameter ranges may be motion parameter ranges, sound parameter ranges, and the like. The feedback based control mechanism may provide motion feedback to control the motion of the swing of the infant calming/sleep aid device 2258. The motion feedback may activate a calming reflex of the infant to provide vestibular stimulation in the inner ear of the infant. The feedback based control mechanism may operate as a feedback loop. The feedback loop may result in a reduction overtime of the mechanism to activate the calming reflex or conditioned response of an infant. For example, it may be desirable to wean an infant from the motion of the infant calming/sleep aid device 2258 starting when the infant is of the age 3-4 months. The feedback based control mechanism may be activated by a remote control, a camera mounted on the infant calming/sleep aid device 2258, and the like. The remote control may be operated by a parent. The parent may be in the same room as the infant calming/sleep aid device 2258, or a different room than the infant calming/sleep aid device 2258.

The infant calming/sleep aid device 2258 may provide analytics and algorithms. The analytics and algorithms may be based on readings from microphone, sensors and the like. The analytics and algorithms may provide feedback input to the mechanism to activate the calming reflex of an infant. The algorithms may analyze combinations, store combinations, replicate combinations and the like. Sensors may provide sensor readings. Sensor readings may have ranges. A range may be a sound range, a motion range, and the like. A sound range may be based on the blood flow/heartbeat of a mother. The heartbeat may be 80 bpm, 160 bpm, 240 bpm, and the like. The motion range may be between 0.5-4.25 Hz.

The analytics and algorithms may be used to detect if an infant is upset or has apnea. The detection may be based on visual inspection, continuous detection, and the like. Visual inspection may be used to initiate a calming mechanism involving a relatively step wise and high frequency motion. Continuous detection may shift into a remain calm protocol, may use a sensor, and the like. A sensor may detect if the infant is in the infant calming/sleep aid device 2258, detect if the secure sleep sack is properly attached to the infant calming/sleep aid device 2258 and the like. The mechanism may only turn on if the sensor detects that the sleep sack is properly installed in the infant calming/sleep aid device 2258.

The infant calming/sleep aid device 2258 may provide an application programming interface (API). The API may allow integration of the infant calming/sleep aid device 2258 with external devices and system. External devices and systems may provide additional control inputs to activate the mechanism to activate the calming reflex or conditioned response of an infant. The mechanism to activate these infant responses may provide inputs to the external devices and systems. Control inputs may include sound control inputs. Sound control inputs may be used to turn on and off external sound sources, turn on and off sound sources internal to the sleep aid device mechanism, and the like. The sound control inputs may provide the user the ability to choose which sound sources to activate and even to introduce their own novel sounds, such as a recording of a parent's voice. Integration may be by wired or wireless connectivity. Wired connectivity may include the use of a hard-wired splitter. Wireless connectivity may include Wi-Fi connectivity, blue-tooth connectivity, and the like. External devices and systems may be home automation network external devices and systems and allow integration of the infant calming/sleep-aid device 2258 with a home automation network. Integration with the home automation network may enable the infant calming/sleep-aid device 2258 to report to a user or allow the user to remotely control the infant calming/sleep-aid device 2258, e.g., via a remote user device. Integration may include integration with monitors comprising sensors 2002. Monitors may include carbon monoxide monitors, oxygen level monitors, breathing monitor, oxygen saturation monitors, motion monitors, temperature monitors, smoke monitors, heart rate detector monitors, respiratory rate monitors, and the like. Monitors may provide an input to activate the sleep aid device 2258 that may activate the sleep aid device 2258. The infant calming/sleep aid device 2258 may be activated to attempt to wake an infant, such as by stimulation with vigorous motion or loud sound or both. An infant may be stimulated to prevent sudden infant death syndrome (SIDS). Integration may also include integration with safety systems. Safety systems may include home safety systems, infant safety systems, child safety systems, and the like.

The sleep aid device 2258 may also include collapsible walls and legs, handles, cord, wheels, and the like. Collapsible walls may enable portability and adjustability. Portability may include ease of moving the sleep aid device 2258 around a room, facilitate shipping, travel, aging of the baby, a standing position, user or stroller height, and the like. Cord may be a retractable cord, a break-away cord, and the like. Wheels may be implemented when collapsed, and the like. Legs may be extendable, telescoping, collapsible or removable and rotated/reinserted to be a different height, and the like. The sleep aid device 2258 may be made available in a lightweight embodiment, include a stand trolley, and the like. Stand trolley may include wheels for inside transport, make the sleep aid device 2258 reconfigurable into a stroller, provide stability, motor removal, enable transportability, and the like. Stability may include stability during motion, stability during strolling, and the like. The sleep aid device 2258 may be made available in a variety of colors and color combinations. Color and color combinations may be user selectable and may be changeable via alternative veneers, alternate ornamental fabric decoration strips, mesh color/design, sleep sack color/design, and the like. The sleep aid device 2258 may be made available in organic materials, appealing designs, and the like. The sleep aid device 2258 may be certified for safety, certified for safety in many categories, and the like. The sleep aid device 2258 may have removable mesh that allows for creating individually selected designs printed on the outside mesh. The accelerometer 2223 of the sleep aid device 2258 may measure head excursions to prevent excessive motion, and the like. The sleep aid device 2258 may be made include flexible mesh. Flexible mesh may provide better airflow and allow broader excursions of the platform. The flexible mesh must be made stiff enough to prevent a pocket forming to potentially suffocate an infant who rolls into it, however flexible enough to allow for give so the top platform may sway back-and-forth. A mattress may include a gel pad on which the head of the infant may rest. A weight sensor may be underneath the gel pad. The sleep aid device 2258 may not activate or may shut off if the weight sensor under the gel pad does not indicate that the head of the infant is resting on the gel pad. The sleep aid device 2258 may include a sleep sack (see, e.g., FIG. 2) that may have an attachment. The attachment may attach the sleep sack to a movable platform (see, e.g., FIG. 2). The sleep sack may be available in different designs. Designs may be printed designs. Printed designs may be non-threatening designs. Non-threatening designs may be animal designs, angel designs, wings, and the like. Designs may be available with options, changeable, engaging, and the like. The sleep sack may be available in various materials. Materials may include a mesh component, be adapted for the seasons, and the like. A mesh component may be a cooling component, a breathable component, and the like. Mesh may prevent overheating and reduces the risk of suffocation. The breathable component may include active airflow to increase breathability. Adaptability for the seasons may include adaptability for warm temperatures, cold temperatures, and the like. The sleep sack may include interior sleeves.

The sleep aid device 2258 may have selectable modes. Selectable modes may be selected with an algorithm. The algorithm set point may be based on the age of the infant. The sleep aid device 2258 may ask for dates of the infant from a user. Dates of the infant may be due date, birth date, and the like. The sleep aid device 2258 may ask the user if the infant was born early, late, and the like. Age of the infant may be based on the age inputs. Age inputs may be dates of the infant, if the infant was born, early, late, and the like. Algorithm set point may be calculated by asking the age of the infant, then subtracting the age of the infant from the birth date of the infant. Algorithm set point may also be calculated by setting the birth date of the infant to the due date of the infant. Age of the infant may be provided in months, weeks, days, and the like.

The sleep aid device 2258 may have a start mode. Start mode may be initiated when the sleep aid device 2258 is turned on to operate and may be based on the age of the infant. Start mode for an infant less than 0 months old may be Baseline and may not go higher than Intervention2. Start mode for an infant that is between 0 and 0.5 months may be Initial1 and may not go higher than Intervention2. Start mode for an infant that is between 0.5 and 3 months may be Initial1. Start mode for an infant between 3 and 4 months may be Baseline or Initial1 if Baseline Boost is active. Start mode for an infant that is older than 4 months may be initial 1 with 1.0 Hz motion and may then use no motion and normal sound in Baseline. Normal sound may be 68 dB Rain on the Roof.

Selectable modes may be modified by a Baseline Boost setting. Baseline Boost setting may be based on the age of the infant. Baseline boost for an infant that is younger than 0 months may not be activated. Baseline Boost setting for an infant that is between 0 and 1 month may cause the sleep aid device 2258 to start in Initial1 when switched on and may use Initial1 settings in Baseline. Baseline Boost setting for an infant that is between 1 and 3 months may cause the sleep aid device 2258 to start with a more robust level of sound, or motion, or both. This level may be equivalent to Initial1 when the device is switched on and may use 1.0-2.0 Hz motion and 70 dB sound settings in Baseline. Baseline Boost setting for an infant that is between 3 and 4 months may cause the sleep aid device 2258 to start in Initial1 with 1.0-2.0 Hz motion setting when switched on and may then use normal settings in Baseline. Baseline Boost setting for an infant that older than 4 months may cause the sleep aid device 2258 to start in Initial1 with 0.5-1.5 Hz motion when switched on and may use no motion and normal sound settings in Baseline. Normal sound may be 68-74 dB Rain on the Roof sound.

When Baseline Boost is set for an extended setting, it may automatically revert to default after 14 days of activation, immediately, and the like. Revert to default immediately may occur when the sleep aid device 2258 is reset for a new infant.

Selectable modes may include Baseline, Intervention1, Intervention2, Intervention3, Intervention4, and the like. Baseline mode settings may be based on the age of the infant. Baseline mode settings for an infant between 0 and 1 month may be 1.0 Hz motion and Rain on the Roof at 70 dB sound, for an infant between 1 and 4 months 1.0 Hz motion and Rain of the Roof at 68 dB sound, for an infant older than 4 months 0.0 Hz motion and Rain on the Roof at 68 dB sound, and the like. Baseline when Baseline Boost is activated for an infant between 0 and 1 month may be 2.0 Hz motion and Rain on the Roof at 72 dB sound, for an infant between 1 and 3 months 2.0 Hz motion and 70 dB Rain on the Roof sound, and the like. Baseline may step up to Intervention1 if Crying_D1 is detected. Crying_D1 may trigger at 0.6 accumulated seconds of Crying Audio Classification time during a period of 6 seconds, and the like.

Intervention1 may be 2.5 Hz motion and Rain on the Roof at 72 dB sound. Intervention1 may step up to Intervention2 if Crying_D1 is detected, otherwise go to CoolDown3 after 8 minutes.

Intervention2 settings may be based on the age of the infant. Intervention2 settings for an infant younger than 0.5 months may be 2.8 Hz motion and Strong Hair Drier sound at 75 dB, may switch to Timeout if Crying_D2 is detected in the last 10 seconds (3:50 to 4:00), otherwise step to CoolDown2 after 4 minutes, and the like. Crying_D2 may trigger at 1.2 accumulated seconds of Crying Audio Classification time in a period of 6 seconds, and the like.

Intervention2 settings for an infant between 0.5 and 1 month may be 2.8 Hz motion and Strong Hair Drier sound at 75 dB, may step up to Intervention3 if Crying_D2 is detected, otherwise go to CoolDown2 after 4 minutes, and the like. Intervention2 settings for an infant older than 1 month may be 3.0 Hz motion and Strong Hair Drier sound at 75 dB, may step up to Intervention3 if Crying_D2 is detected, otherwise go to CoolDown2 after 4 minutes, and the like.

Intervention3 settings may be based on the age of the infant. Intervention3 settings for an infant between 0.5 and 1 month may be 2.8 Hz motion and Fast and Vigorous sound at 79 dB, and the like. Intervention3 settings for an infant older than 1 month may be 3.25 Hz motion and Fast and Vigorous sound at 79 dB, may switch to Timeout if Crying_D2 is detected in last 10 seconds (2:20 to 2:30), present user option to use Intervention4, otherwise Step to CoolDown1 after 2.5 minutes, and the like. CoolDown1 settings may be based on the age of the infant. CoolDown1 settings for an infant between 0.5 and 1 month may be 2.8 Hz motion, Strong Hair Drier 75 dB sound, for an infant older than 1 month 3.0 Hz motion and Strong Hair Drier 75 dB sound, and the like. CoolDown1 may step up to Intervention3 if Crying_D2 is detected, otherwise go to CoolDown2 after 4 minutes, and the like. CoolDown2 may be 2.5 Hz motion and Strong Hair Drier sound at 72 dB and the like. CoolDown2 may step up to Intervention2 if Crying_D2 is detected, otherwise go to CoolDown3 after 8 minutes, and the like. CoolDown3 settings may be 1.8 Hz, Rain on the Roof sound at 70 dB, and the like. CoolDown3 may step up to Intervention1 if Crying_D2 is detected, otherwise got to Baseline after 12 minutes, and the like.

Intervention4 may be only manually activated. Intervention4 settings may be based on the age of an infant. Intervention4 settings for an infant between 0.5 and 1 month of age may be 2.8 Hz Fast and Vigorous at 81 dB sound, for an infant older than 1 month 3.25 Hz Fast and Vigorous sound at 85 dB, and the like. Intervention4 may switch to Timeout if Crying_D2 in last 10 seconds (1:50 to 2:00) is detected, otherwise return to regular operation by auto-stepping to Intervention3 after 2 minutes, and the like.

Timeout may be no alarm, alarm noise then silence, and the like. Alarm noise may be 6 beeps with 1 second timing between beeps, 4 second pause, 3 beeps with 1 second timing between the beeps, and the like. Timeout may also include an LED. LED may be a red LED, flashing until the sleep aid device 2258 is reset by the user, and the like.

The sleep aid device 2258 may include other safety mechanisms that may impact the selection and activation of the operational modes. Other safety mechanisms that may impact the selection and activation of the operational modes may include shutting off if Intervention3 has ended and the infant is still crying, shutting off if Intervention4 has ended and the infant is still crying, not starting if the sleep sack is not properly engaged, not starting if the infant's head is not sensed to be in the proper location, stopping if the infant's head is sensed to no longer be in the proper location, not starting if the sleep aid device 2258 has been activated for longer than 6 hours in the day for the first two months, may not start if a sensor detects that the baby is not aligned properly in the sleep aid device 2258, and the like. If the sleep aid device 2258 has shut off because either Intervention3 or Intervention4 has ended and the infant is still crying, the sleep aid device 2258 may be reset, in order to allow the sleep aid device 2258 to be activated again.

The sleep aid device 2258 may include protocols, profiles, components, and add-on's. Protocols may be based on the age of the infant and how upset the infant is. Protocols may be based on functions. Functions may be motion functions, sound functions, light indicator functions, ambient light sensor functions, light generation functions, or combinations of functions. Light indicator functions may be a night light, an indicator to provide a warning to a user when the user is shaking the sleep aid device 2258, an indicator to signal which intervention levels are being delivered, and the like. The indicator to provide a warning to a user when the user is shaking the sleep aid device 2258 may indicate that the level of shaking may be unsafe. Light indicator functions may be integrated with the sleep aid device 2258, displayed on a connected device, and the like. A connected device may be a smartphone, tablet computer, and the like. Ambient light sensor functions may be integrated with the sleep aid device 2258, located on a connected device, and the like. Light generation functions may be functional, aesthetic, and the like. Functional light generation functions may illuminate the user interface of the sleep aid device 2258, provide an orange melatonin inducing night light, and the like. Profiles may be based on knowledge of an infant profile, user override using preferences, and the like. User override may provide the user with several choices to override and raise the baseline intervention. Components may be cords, batteries, motors, and the like. Cords may be breakaway cords, retractable cords, and the like. Batteries may be rechargeable as an option for sound, and the like. Add-on's may be cameras, scales, measuring devices, a kit for turning the infant calming/sleep aid device 2258 into a crib, playpen, or the like, extra blankets, sheets, skins, parts, a travel bag, and the like.

The sleep aid device 2258 may facilitate interface integration. Interface integration may facilitate integration with interfaces such as Bluetooth interfaces, hard-wired interfaces, home automation network interfaces, monitors, and the like. Hard-wired interfaces may include hard-wired splitter interfaces. Monitors may include carbon monoxide monitors, safety monitors, and the like. Safety monitors may include home safety monitors, baby safety monitors, child safety monitors, and the like.

The sleep aid device 2258 may comprise a user interface. The user interface may comprise a control panel. The control panel may control options such as motor speed, modulation, speaker output, and the like. The control panel may comprise knobs, switches, lights, motion activation, sound activation, interfaces to drive electronics and other I/O methods.

The sleep aid device 2258 may comprise sub-assembly components. Such components may comprise amplitude modulation components, screws, gears, nut frames, springs, and the like.

The sleep aid device 2258 may comprise a head platform. The head platform may passively rotate. The head platform may comprise a spring system using injection molded plastic as the spring/damper to reduce noise and parts required. The head platform may comprise a plurality of dampers. The head platform may comprise a covering. The cover may be flexible, cloth, foam, or the like. The head platform may comprise joint connectors, such as, but not limited to, hinge and rod connectors. The head platform may comprise bearings such as, but not limited to rotation and head rotation bearings. The head platform may comprise wraps. The wraps may comprise swaddling wraps, fastening wraps, and the like.

The sleep aid device 2258 may comprise an enclosure around a sleep surface. One embodiment may have a light mesh veil/mosquito netting over the top of the device. One embodiment may have an ornamental animal head and tail that may be attached onto the device. The sleep surface may comprise a position stabilizer. The surface may secure a baby in supine position to prevent unraveling or rolling and to maintain optimal stimulation positioning. The sleep aid device 2258 may comprise a single head platform which may passively rotate and which may be constrained by springs or dampers. The sleep surface body platform made from flexible cloth covering or flexible foam padding. In embodiment, the sleep surface may comprise a movable joint connector using hinges, rods, or the like. In embodiments, the sleep surface may comprise a support platform. In embodiments the sleep surface may comprise bearings. In embodiments, the sleep surface may comprise a special head insert to reduce pressure on back of skull. In embodiments, the sleep aid device may comprise adjustable legs allowing variable height configurations. In embodiments, the sleep surface may comprise a secure sleep sack. In embodiments, the sleep surface may interact with an electronically programmable interface system. The interface system may comprise a control panel (see, e.g., FIG. 1). The control panel may comprise switches, lights, and other I/O interface capabilities. The interface system may comprise automated programming selections or may allow a user to select device settings, such as duration. In embodiments, the sleep surface may comprise drive electronics to control drive motor speed, an amplitude modulation motor, and speaker audio output. Speaker outputs may comprise specified equalizer settings i.e. the use of special sound profiles to promote sleep and reduce crying. In embodiments, the sleep surface may comprise plates such as drive plates or swing arm plates, among others. In embodiments, the sleep surface may comprise a push or pull rod. In embodiments, the sleep surface may comprise drive motor connections to different drive types such as clamps, bearings, pins, among others. In embodiments, the sleep surface may comprise an elastic actuator catch bracket. In embodiments, the sleep surface may comprise a sub-assembly to directly control the amplitude output of the main rotating platform. The sub-assembly may comprise components such as, but not limited to, amplitude modulation rotational bearings, acme screws, acme nuts, acme nut frames, and gears. In embodiments, the sleep surface may comprise an amplitude modulation motor.

The sleep aid device 2258 may comprise a motion generation and drive mechanism for a crib. The mechanism may comprise an electronic motor. The motor may be isolated from proximity to the baby for EMR shielding. The mechanism's movement may take into account wear and tear. The mechanism may comprise elastic walls to move with the mattress. The mechanism may comprise a swing arm crank shaft either directly or indirectly attached to the motor. The mechanism may comprise a plurality of springs such as injected plastic springs. The mechanism may have stability components in order to compensate for interactions with the stand and the environment. The mechanism may move in a sinusoidal motion when the infant is asleep and a nonsinusoidal motion when the infant is awake or crying, to attempt to calm the child down. The mechanism may operate with a direct amplitude adjustment or may operate without such direct adjustments. Direct amplitude adjustment settings may comprise a slow and large amplitude setting (e.g. 30 cycles per minute and 6 cm/cycle at the head), a fast and short amplitude setting (e.g. 150 cycles per minute and 3 cm/cycle at the head), a rapid and short amplitude setting (e.g. 180 cycles per minute and 2 cm/cycle at the head, among other combinations (e.g. 4.5 Hz, 270 cpm, range 150-270 cpm). The mechanism may comprise an accelerometer in order to measure head movement. In embodiments, the mechanism may work in conjunction with sensors placed under a mattress to detect when or if an infant is in the crib without being secured in the sleep sack. The mechanism may stop movement if the sensors detect that the infant is in a compromised position or if the infant is no longer in the sleep sack. Movement may also stop when a calming movement mode has been completed and the infant is still crying. In embodiments, users may not be able to manually select movements and may warn users if safety parameters are not met, such as excessive acceleration or unsafe frequency. In embodiments, a manual override may be provided to uncouple the motion generator if a motion is undesirable The sleep aid device 2258 may comprise a crib sound system. In embodiments, equalizer settings may be provided for optimal pitch profiles (e.g. sound levels are mixed with increasing high pitch profiles as a baby cries more). The sound system may comprise speakers and may generate sounds similar to those hard by the babies in utero. For example, sounds may be generated to replicate the turbulence of blood flowing through uterine and umbilical arteries. In embodiments, the high frequency component may be diminished (e.g. 65 to 70 dB with a profile predominantly about <500 Hz). In other embodiments, the system may be capable of a harsher sound (e.g. 70 to 75 dB with a profile predominantly about <1000 Hz) or a multi-frequency sound (e.g. 75 to 80 dB with a profile from 0 to 16000 Hz). In embodiments, the system may be calibrated not to exceed 85 dB at the infant's head, not to exceed more than 18 hours a day to prevent overuse and not to exceed 85 dB for longer than 20 minutes of an hour. If such levels are exceeded, a notification may be provided to a user in order to stop usage. In embodiments, the speaker may make an alarm sound when the device times out. In embodiments, the sound system may comprise variable volume controls. In embodiments, the sound system may be able to detect sounds. Such detections may be conducted by microphones to sense warnings, to hear a child, or to indicate the duration a child has been crying, among other uses. The sound system may be used to conduct analysis on such detections. In embodiments, the sound system may be battery operated. Sounds may be imported into sound interface applications, such as Dolby Advanced Audio v2, to provide music, voices, singing as an overtone, or interactively talk to the infant via the application API. In embodiments, the sound system may be removed or dampened.

In embodiments, the sleep aid device 2258 or control system 2216 thereof may comprise microprocessors for use controlling the operations of the sleep aid device 2258. Microprocessors may be used to differentiate sounds, such as infant sounds, system sounds, or ambient noise. Microprocessors may be used to record and analyze sounds. Such sounds may include sounds which reflect a baby's state (e.g. sleeping, crying) or to provide feedback. Microprocessors may be used to generate responses and deliver the optimal mix of sound and motion for a specific. For example, a user may implement an initial combination of sound and motion for the first few uses, then switch to a different program based on a child's reaction to the uses. Microprocessors may be used to respond to changing states, such as to calm crying, reduce sleep latency, increase sleep efficiency, among others. Microprocessors may also be used to wean infants off of motion and sound as they age. For example, the device may increase sound and motion as child gets older and then automatically wean the baby off motion as he or she gets over 4 months. The electronic data processor described herein with respect to the control system may include one or more microprocessors. The device may also react to incidents of waking and reduced crying. Microprocessors may take in inputs such as the weight of an infant, age of infant, whether the infant was delivered on time, the duration of detected sound made by infant, the duration of detected motion of infant, the desired motion state, the sensed motion frequency, the amplitude of main platform, the desired system speed, whether motion of main rotating platform exceeds safety threshold, and the like. The microprocessor may generate outputs such as motor control, audio responses and visual signals.

The sleep aid device 2258 may comprise a mechanism for the more square waveform generation. Such a mechanism may be enabled by flexible joint connecting head and body platform. The main rotating platform may use a variety of variables to determine the waveform generation, such as weight of infant, drive motor frequency, balancing compression spring force constant, as well as other variables.

The sleep aid device 2258 may rely on several algorithms in order to generate outputs to calm an infant. The device may analyze certain output combinations that have succeeded, store such combinations, and then replicate these combinations. The device may create profiles based on knowledge of a child's physiological or behavioral parameters or based on a parent or user's overrides and preferences, among a variety of other parameters.

The sleep aid device 2258 may comprise a motion analysis module. The module may comprise a motion amplitude estimate signal, a threshold-crossing based motion frequency estimator, a time-based filter, a digital filter bank, a filtered accelerometer data signal, and a motion frequency estimate signal among others. The sleep aid device 2258 may comprise a behavior state machine module, an audio generation module, a crying detection module, and the like. The crying detection module may comprise a digital bandpass filter and a time-based filter.

The sleep aid device 2258 may comprise a mattress for a crib. The mattress may be made from organic materials such as organic latex, coconut fiber, or polyethylene, and may comprise a gel pad for the head. The mattress may be created for firmness or softness preferences, and may also be waterproof. Compatible sheets may be used for the mattress and the mattress may contain circuitry so that it may maintain connectivity with walls, the mattress, and the platform.

The sleep aid device 2258 may be controlled remote by smartphone or other mobile device using communication standards such as Bluetooth. The sleep aid device 2258 may comprise variable motion and sound capabilities as well as a feedback loop and mechanisms to reduce functionality over time. The sleep aid device 2258 may comprise a moving platform and may have a dual range of motion. The sleep aid device 2258 may comprise a plurality of collapsible walls and legs. Such functionality may aid in shipping, travelling, aiding a child to stand, among other uses. The functionality may change depending on the age of the infant or the stroller height/height of the baby's mother. The sleep aid device 2258 may comprise handles, wheels, and legs that may be extendable, adjustable, or collapsible. The sleep aid device 2258 may comprise trolley functionality to transform the device into a stroller or it may comprise a crib functionality to transform the device into a crib. The sleep aid device 2258 may comprise wheels for transport. The sleep aid device 2258 may comprise a removable motor. The sleep aid device 2258 may comprise flexible and removable mesh components. One embodiment envisions the ability to re-obtain back units and refurbish them to resell on a secondary market.

In embodiments, the sleep aid device 2258 may generate a plurality of outputs. Such outputs may be user modes such as movement modes. Movement modes may comprise short and large amplitude modes, fast and short amplitude modes and rapid and short amplitude modes, among others. Outputs may also comprise sound modes such as modes where the high frequency component is diminished, modes that produce a harsher sound and modes that produce a multi-frequency sound.

As introduced above with respect to FIG. 11A, the sleep aid device 2258 may comprise sensors 2002 such as, but not limited to, audio sensors, motion sensors, biometric, a camera, other third party sensors, flexible sensors, accelerometers, a warning system, and a manual override. The sleep aid device 2258 may comprise sensors 2002 or components such as a camera, a scale, an ambient temperature thermometer, a heart rate monitor, a respiratory rate monitor, an oxygen monitor, a measuring device, a kit for turning the device into a crib, a kit for turning the device into a playpen, extra accessories, a microphone, and sound importing capabilities, such as music, voices, singing, and interactive talking via an API. In embodiments, device components may be removable. The sleep aid device 2258 may comprise an electrical cord that may be able to break away or may be retractable. The sleep aid device 2258 may comprise batteries, and in embodiments, batteries which may be rechargeable. The sleep aid device 2258 may comprise light indicators such as a night light, or a shaking detection light, ambient light sensors, functional lights (e.g. to light up the user interface, to induce melatonin, to assess manual jiggle, to function as a stroller light), and lights to signal that an intervention level is being delivered. The sleep aid device 2258 may comprise several different aesthetic features, such as changing designs.

The sleep aid device 2258 may employ a plurality of different parameters. In embodiments, sound and motion ranges may be restricted. In embodiments, the device may use different thresholds or triggers to deliver output. Such triggers may include sensory inputs, behavioral inputs, variational inputs, head movement, acceleration, frequency, amplitude, rotation, safety, number of waking incidents, number of crying incidents, abnormal biometric readings and an infant's measurements, among others. Such triggers may be calculated based on the individual infant's history using machine learning. Variational inputs may include individual variations, optimal stimulus level data, and state data such as type of sleep, drowsiness, quietness, fussing, or crying. The sleep aid device 2258 may rely on duration inputs for sound and motion. The sleep aid device 2258 may rely on target inputs such as desired motion state or desired system speed. The sleep aid device 2258 may rely on noise detection from the system, infant, or ambient noise and also rely on biometric sensors. The device may differentiate between multiple types of noise. The sleep aid device 2258 may rely on filters such as band-pass, digital band-pass, time-based, a filter bank, or a digital filter bank, among others. The outputs, such as sound and motion, may be predicted based previous behavior of the infant or a group of infants, using artificial intelligence algorithms.

The sleep aid device 2258 may be deployed for several uses such as, but not limited to monitoring, reporting, control, analytics, reports/statistics, sharing/groups, benchmarking/comparison, graphics, acoustic signature of the cry, organizational data, expert feedback, communications (e.g. walkie-talkie), providing alerts (e.g. warning alerts, health concern alerts), overtone customization of the white noise, photo/video/audio input, journal sharing/printout, automatize diaper/formula ordering online, weight determination, breastfeeding determination, and image capturing uses, among others.

The sleep aid device 2258 may be integrated to work with a smartphone or other similar mobile device. The device may communicate with the mobile device using methods such as USB, Bluetooth, and Wi-Fi, among others. The mobile phone may be used to input information such as weight (at birth and longitudinal weight), length (at birth and longitudinal), head size (at birth and longitudinal), the frequency of feeding, frequency of diaper changes and sleep behavior, among others. User may be able to use their mobile device to instantly create and share graphic displays of their baby's sleep pattern over different periods of time, among many other uses.

As introduced above, a sleep aid system 2000 may include a smart power hub 202. In various embodiments, the sleep aid system 2000 further include or operatively associates with a sleep aid device 2258, such as the sleep aid device described herein.

The smart power hub 202 may be configured to provide network and data communication services with respect to the sleep aid device 2258 and remote devices, such as remote user interfaces, update devices, and the like. In some embodiments, the smart power hub 202 may also comprise a power system 208 including A/C to D/C conversion and D/C to D/C functions.

Figure 12:
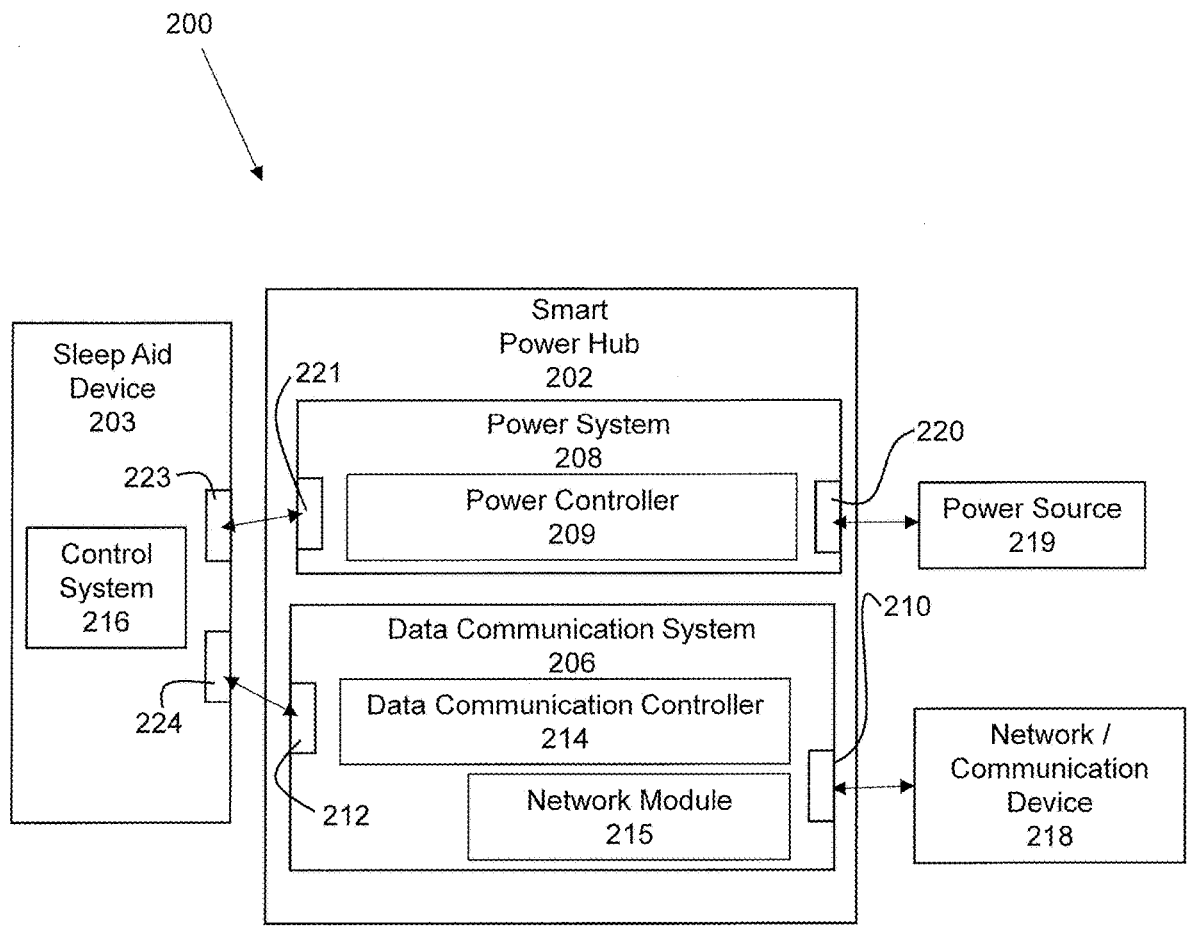
FIG. 12 schematically illustrates a sleep aid system including a smart power hub according to various embodiments described herein.

FIG. 12 is a diagram illustrating operation of a sleep aid system 200. The sleep aid system 200 may be similar or include similar components and/or functions as described above with respect to sleep aid system 2000 described with respect to FIGS. 11A & 11B. The sleep aid system 200 includes a smart power hub 202 that operatively connects to a sleep aid device 203. The sleep aid device 203 may be a powered sleep aid device 203 including a movable platform. In some embodiments, the sleep aid device 203 may be any of the sleep aid devices described herein with respect to FIG. 1-11B or elsewhere herein. The sleep aid device 203 includes a control system 216 for controlling operations of the sleep aid device 203. In various embodiments, the control system 216 may be similar or include similar components and/or operations as described above with respect to control systems 120 and 2216 (see FIGS. 3-11B).

In various embodiments, the smart power hub 202 may couple between a power source 219 and the sleep aid device 203 to provide power to the sleep aid device 203. For example, the smart power hub 202 may include a power system 208. The power system 208 may include a power controller 209 with functions such as A/C to D/C conversion, with further D/C to D/C conversion as needed, as well as any safety and protection circuits required. However, in other embodiments, the smart power hub 202 does not include a power system 208 having such functionalities and the sleep aid device 203 may include an onboard power supply/AC adaptor. It will be appreciated, that in some embodiments, various functionalities of the smart power hub 202 may be distributed, e.g., embodied in separable hardware units or structures. For example, power functions may be provided in a power brick that couples to the sleep aid device 203 while data communication functions may be provided in a separate smart power hub unit that couples to the sleep aid device 203.

As introduced above, the sleep aid device 203 may include one or more operations requiring a supply of power. In some configurations, the power may be provided by the power system 208. The power may be supplied continuously, as needed, periodically, or combination thereof. The power system may also provide different voltages from time-to-time, as requested by the sleep aid device 203. For example, the sleep aid device 203 may be required to power various devices and operations which may include one or more of movement of a platform, such as powering one or more motors configured to move the platform; one or more sensor devices for detecting platform motion, platform sound corresponding to motion of the platform, infant motion, infant sound, infant motion, ambient sound, ambient light, environment motion; a sound device for outputting sound such as alarms, music/songs, meditative sounds, noise block, white noise, notifications, recorded or contemporaneous sound provided by a user; camera or other imaging device; a display device, which may include a projector or screen for display of images or video; a local or remote user interface; one or more peripheral devices which may any of the above devices; data storage devices, e.g., computer readable storage mediums or digital data storage hardware, or data storage, e.g., firmware, software, programs, applications, collected data, archival or collected data or analysis of collected data, retrieval of collected data; a communication system including a receiver, transmitter, or transceiver for receiving data from the smart power hub 202 or a user device such as user interaction data, software/firmware updates, and the like, and transmitting data to the smart power hub 202 such as collected infant or analyzed infant data, status updates, user media, and the like; control system 216 for controlling one or more operations of the sleep aid device 203; a processor for executing instructions for controlling the one or more of the operations of the sleep aid system 200.

The power system 208 may include a power controller 209 configured to control power delivery, power regulation, and/or power conversion. The power system 208 may couple to a supply of power 219, such as an electrical outlet, through a wired connection from a first power port 220 and transmit power to the sleep aid device through a wired connection between a second power port 221 and a power port 223 of the sleep aid device 203. In some embodiments, the sleep aid device 203 may include energy storage that may be charged by the power system 208. Sleep aid device 203 may utilize the battery as a primary, secondary or backup energy source. For example, the sleep aid device 203 may utilize the battery for travel operation or emergency backup. In one such embodiment, the power system 208 may include charging functions configured to charge the battery. In one example, the infant sleep aid device 203 does not include a battery.

The smart power hub 202 may include a data communication system 206 configured to receive and transmit data and commands. The data communication system 206 may provide wired, wireless, or both wired and wireless communication. The data communication system 206 may include a first data communication port 210 and a second data communication port 212. The first data communication port 210 may include a receiver or transceiver for receiving data communications from a remote device via a wired or wired connection. The first data communication port 210 may be coupled to a wired or wireless transmitter or transceiver for transmitting data communications 215 and is connected to one or more communication networks 218. The first data communication port 210 may transmit data, receive data, or otherwise be in data communication with a network 218. In one example, the first data communication port 210 is in data communication with a communication device comprising a modem via a wired or wireless connection for receiving and/or transmitting data communication through a network, e.g., an internet or cellular network. Wireless communication may include WiFi technology, for example. In some embodiments, the Network module 215 may be configured for wireless communication utilizing Bluetooth/BLE or WiFi standard.

The second data communication port 212 may typically include a receiver, transmitter, or transceiver for receiving and transmitting data communications between the sleep aid device 203 and the smart power hub 202. The second data communication port 212 will typically couple to the sleep aid device via a wired connection. In one embodiment, the second data communication port 212 may be configured to communicate with the sleep aid device 203, control system 216 thereof, or an associated sensor via wireless communication.

The data communication system 206 may also include a data communication controller 214. The data communication controller 214 may be configured to handle data between the data communication ports 210, 212. The sleep aid device 203 may include a data communication port 224 for data communication with the data communication system 206 via the second data communication port 212 for transmission, reception, and/or exchange of data. In some embodiments, power port 221 and data communication port 212 and/or power port 223 and data communication port 224 may share a connection.

The data communication system 206 may further include a network module 215 configured to provide communications services and communicatively link to one or more networks/communication devices 218 via communication port 210, which may include or be configured for operation together with the first and/or second data communication ports 210, 212. In some instances, the data communication controller 214 and network module 215 may be the same instance. In various embodiments, the network module 215 may be configured for wired or wireless data communication directly or indirectly, e.g., via an intermediate networking or communication device or network, with communication devices. For example, the network module 215 may be configured to establish, join, or communicate with one or more networks. In a further or another example, the network module 215 may be configured for wired and/or wireless communication via landlines, routers, switches, internet, Ethernet, cellular, gateways, WiFi, Bluetooth, and/or other wired and/or wireless communication technologies and associated devices for implementing the same.

The network module 215 may include a wireless microcontroller and/or wireless network processor. The network module 215 may include a controller, system of chip (SoC), microcontroller unit (MCU) or other controller configuration for providing control operations of network communications. In some embodiments, the data communication controller 214 may provide all or a portion of control of wireless communication operations. The network module 215 may include hardware for executing data communication operations utilizing various data communication technologies and/or protocols. For example, the network module 215 may include a WiFi technology chip or device for connecting to a wireless device or wireless access point a cellular chipset or module for connection to cellular networks, or both. In a further or another example, the network module 215 may be configured for Ethernet-over-Power (Powerline) or Ethernet.

Network module 215 may include one more of a wireless receiver, transmitter, or transceiver for receiving and/or transmitting data communications via wireless communication. The network module 215 may include a wireless transmitter to transmit data communication to one or more networks and/or communication devices 218, which may include wired or wireless networks such as distributed, local area, wide area, personal area, and/or cellular, and which may be ad hoc, peer-to-peer, mesh, structured, or unstructured, and/or devices such as routers, modems, gateways, switches, user interfaces, user devices, or combinations thereof. Wireless communication or wireless networks may utilize WiFi technology, Bluetooth technology, Bluetooth Low Energy technology, cellular technology, or wireless USB, for example. The network module 215 may comprise all or a portion of the data communication port 210.

Figure 13:
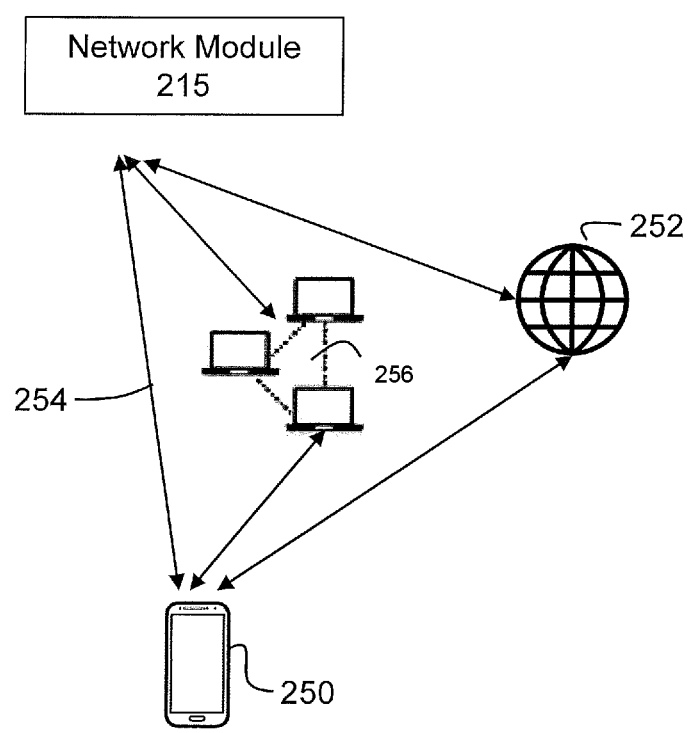
FIG. 13 schematically illustrates a wireless access points provided by a network submodule according to various embodiments described herein.

With further reference to FIG. 13, illustrating various wireless access points or wireless communication paths the network module 215 may provide to a user interface or user device 250, e.g., a smart device, tablet, computer, dedicated device, or the like, the network module 215 may be configured to provide access via an internet 252 connection, which may include communication through a modem for example, an area network 254 comprising a wide, local, ad hoc, or peer-to-peer network, and/or a personal area network 256. It will be appreciated that in some embodiments, such networks may include combinations and/or derivatives of the above networks. In one embodiment, the network module 215 includes WiFi and Bluetooth/Bluetooth Low Energy (BLE) technology solutions, which, for example, may be provided on one or more chips. For example, a personal area network 256 may be provided by a Bluetooth/BLE technology solution and local area network 254 and/or internet 252 access points may be provided by WiFi technology solutions. In one example, user device 250 comprises an application or program configured for communication and interaction with the sleep aid device 203 via the data communication system 206.

In some embodiments, the smart power hub 202 (data communication system 206 or network module 215) may comprise a network node of a network 252, 254, 256 to which the data communication system 206 communicates with via a wired or wireless link or may provide data to a node of the network 252, 254, 256 or directly to a user device 250 or other communication device, which may itself comprise a node or otherwise directly or indirectly transmit the data to a node of a network 252, 254, 256. In one example, the smart power hub 202 comprises a network node that provides access to the sleep aid device 203.

In various embodiments, the data communication system 206 or network module 215 thereof may comprise of wired or wireless routing, switching features, modem, switching, or gateway features. In some embodiments, the communication system 206 may include a wired connection for coupling to a router or modem, for example, to access local or distributed networks. In one implementation, the network module 215 may provide a wireless, e.g., a WiFi technology, connection. Such a wireless connection or another wireless connection may be used to transfer device status with respect to the sleep aid device 203. In further examples, the connection may be used to support media content such as continuous transmission of 1080p video and streaming audio. A local, ad hoc, peer-to-peer, or personal area network connection, e.g., utilizing network 254 or 255 access point or associated paths may also be utilized for media support content or to provide secured access or configuration settings. However, in some embodiments, the internet 252 access point or associated paths may be utilized for media support content or to provide secured access or configuration settings. In one such example, Bluetooth/BLE technology support may be used for in-app authentication, WiFi technology configuration, e.g., including passing credentials. Further applications may include control of motion, sound, or other operations of the sleep aid device from a user device or interface, e.g., from a BLE connected peripheral device. Additional applications may include the sleep aid device 203 providing diagnostic, performance and/or usage information using Bluetooth/BLE technology to device 250 that may further pass the information to internet 252, which may include an internet-based backend.

As introduced above, the sleep aid device 203 may include one or more sensors for monitoring and collecting infant data, which in some embodiments may include data associated with the sleep aid device data. The infant data may be stored or analyzed for current or future use. The infant data may be analyzed to determine a current status of an infant, e.g., soothed, agitated, asleep, or emergency state, as described herein. The analysis may include data comparison with historical data collected with respect to the infant as well as threshold analysis with respect to established parameters. For example, detection of a heart rate, breathing rate, or breathing depth below a threshold may trigger determination of an emergency state. The sleep aid device 203 may transmit all or a portion of the infant data comprising collected or analyzed infant data or determined infant status to the smart power hub 202 for storage or further delivery to a remote device. For example, the sleep aid device 203 may include a control system 216, which may be similar to control system 120 (see, e.g., FIG. 3) and/or control system 2216 (see, e.g., FIG. 11) described above and elsewhere herein. The control system 216 may be configured to output the infant data, e.g., via a data communication port 224 of the sleep aid device 203, to the second data communication port 212 of the data communication system 206.

The data communication system 206 may transmit the infant data, such as infant images, infant sounds, collected infant data comprising hear rate, breathing rate, or motion data, analyzed infant data, infant status, historical infant data, sleep aid device current state, or historical sleep aid device actions or states, as examples. The communication from the sleep aid device 203 may specify actions or routing instructions or such may otherwise be determined by the data communication controller 214. For example, the infant data or an associated communication thereof may include routing instructions such as transmission technology/protocol, e.g., wired, wireless, cellular, WiFi, Bluetooth/BLE. Data transmissions may include network identification, network address, device identifier, device numbers, or the like, such as those with respect to a personal, ad hoc, local or distributed network, user device identifier, application identifiers, programs, or IP addresses. In one example, the data communication controller 214 may be configured to analyze the communication and determine routing protocols. In one embodiment, the communication system 206 may route all communications to one or more destinations, such as an IP address, which may act as a depository and/or routing point for further transmission of all or a portion of the data. A program, application, and/or application programming interface (API) may be utilized for routing and/or interaction with infant data, smart power hub 202, and/or sleep aid device via an external device. In various embodiments, the data communication system 206 may transmit a communication to emergency personnel, social media, archival storage device, which may include cloud storage, or a user interface or device such as a smart device, e.g., phone, tablet, computer, dedicated device, or the like.

In one embodiment, the data communication system 206 may transmit infant data, to care providers or emergency personnel. The communication may include current infant data, historical infant data, or both. Such infant data may be analyzed or raw. The data communication system 206 may receive data from care providers or emergency personnel to be transmitted to a user interface, which may include a user device, or the infant sleep aid device 203. In one example, the data includes control data for controlling one or more operations of the infant sleep aid device 203 or media data. The data may identify stored media or operation data, e.g., stored in a storage device of the infant sleep aid device 203 or accessible directly or indirectly thereby. In one example, the data may identify an action a caregiver local to the infant sleep aid device 203 is to perform or an operation the infant sleep aid device is to execute, which may include particular movements of the platform, sounds, additional data collection tasks to be performed presently or in the future, modification of infant data collection, analysis, or other operation protocols with respect to the operations of the infant sleep aid device 203. In one embodiment, the data may include media data or identify media data that is stored locally or remotely with respect to the smart power hub 202 or the sleep aid device 203. The data communication system 206 may transmit the data to the sleep aid device 203 and the sleep aid device 203 may use the data to identify media data stored in a sleep aid device data storage device or otherwise accessible by the sleep aid device 203. In one example, media data may be transmitted to the sleep aid device 203 via the data communication controller 214 for presentation by the sleep aid device 203. In another example, the media data may be transmitted to a local or remote user interface, which may include a user device. The media data may be displayed, e.g., projected or presented on a screen, with a display device associated with the sleep aid device 203 or a local or remote user interface. The media data may include video data, sound data, text data, or the like. Sound data, for example, may be transmitted to a speaker for output at the infant sleep aid device or at a local or remote user interface. In one example, sound data may be translated into to text and displayed on a screen of a display device associated with a local or remote user interface. In various embodiments, the media data may instruct a caregiver in providing medical or soothing care for an infant or in taking emergency action.

The data communication system 206 may receive media data transmitted by a user device. For example, a user may transmit recorded or contemporaneous sound or video. The media data may be stored by the data communication system 206 or may be transmitted to the sleep aid device 203. At the sleep aid device 203, the media data may be presented at the sleep aid device 203. For example, images may be displayed with a display device or sound may be generated by a sound device. In a further example, the media data is presented in an audio-visual multimedia display. The presentation of the media data may be instantaneous or approximately instantaneous with respect to receipt of the media data. In another example, the media data may be tagged for presentation at a later time, which may be a set time or upon the occurrence of an event or determined status of the infant by the infant sleep aid device. For example, media data comprising a recording of a caregiver's voice or video may be presented if the sleep aid device 203 determines the infant requires soothing. The presentation may be in addition to or instead of movements of the platform.

In various embodiments, the sleep aid system 200 is configured to receive operation updates. For example, update communications may be received by the data communication system 206 and thereafter transmitted to the sleep aid device 203. Updates may include updates of firmware, software, media or the like. Updates may include or modify operation protocols, communication protocols, sensor configurations, thresholds, infant profiles, peripheral device configurations or extensions, media content, security or privacy settings, sound output programs, platform motion frequencies, for example. In one example, the control system 120, 216 (FIGS. 3 & 12) of the sleep aid device includes an update module. The update module may be configured to receive updates from the data communication system 206 of the smart power hub 202. The data communication system 206 may receive the updates at data communication port 210, which may receive the update data via a wired or wireless communication. In the case of a wireless communication, the network module 215 may comprise all or a portion of the data communication port 210 (FIG. 12). Updates may be transmitted to the data communication system 206 by communication devices or networks connected therewith, for example. In some embodiments, a manufacture or product representative may remotely communicate with the sleep aid device 203 via the data communication system 206. Such communications may include data collection with respect to the operations of the sleep aid device 203 or software or firmware updates, as examples. The manufacturer or product representative may include a program or application executed on a communication device or coupled thereto configured for such communication tasks.

As noted above, the smart power hub 202 may be configured to provide both power and data communication capabilities. Data communication may include wired, wireless, or both wired and wireless communication. For example, the smart power hub 202 may be configured to couple to the sleep aid device 203 via a wired connection and provide one or more wireless connections between the sleep aid device 203 and user interfaces or devices, applications, programs, and/or networks. In some embodiments, the data communication system 206 may also include a wired connection to a network access point instead of or in addition to providing wireless communication. In one embodiment, the data communication system 206 is configured to be in data communication with the sleep aid device 203 via a wireless connection.

In various embodiments, the smart power hub 202 is configured for Ethernet over power (Powerline). For example, the data communication system 206 may transmit data to a power line modem, either directly or indirectly via wired or wireless data communication, or may include a power line modem.

Figure 14:
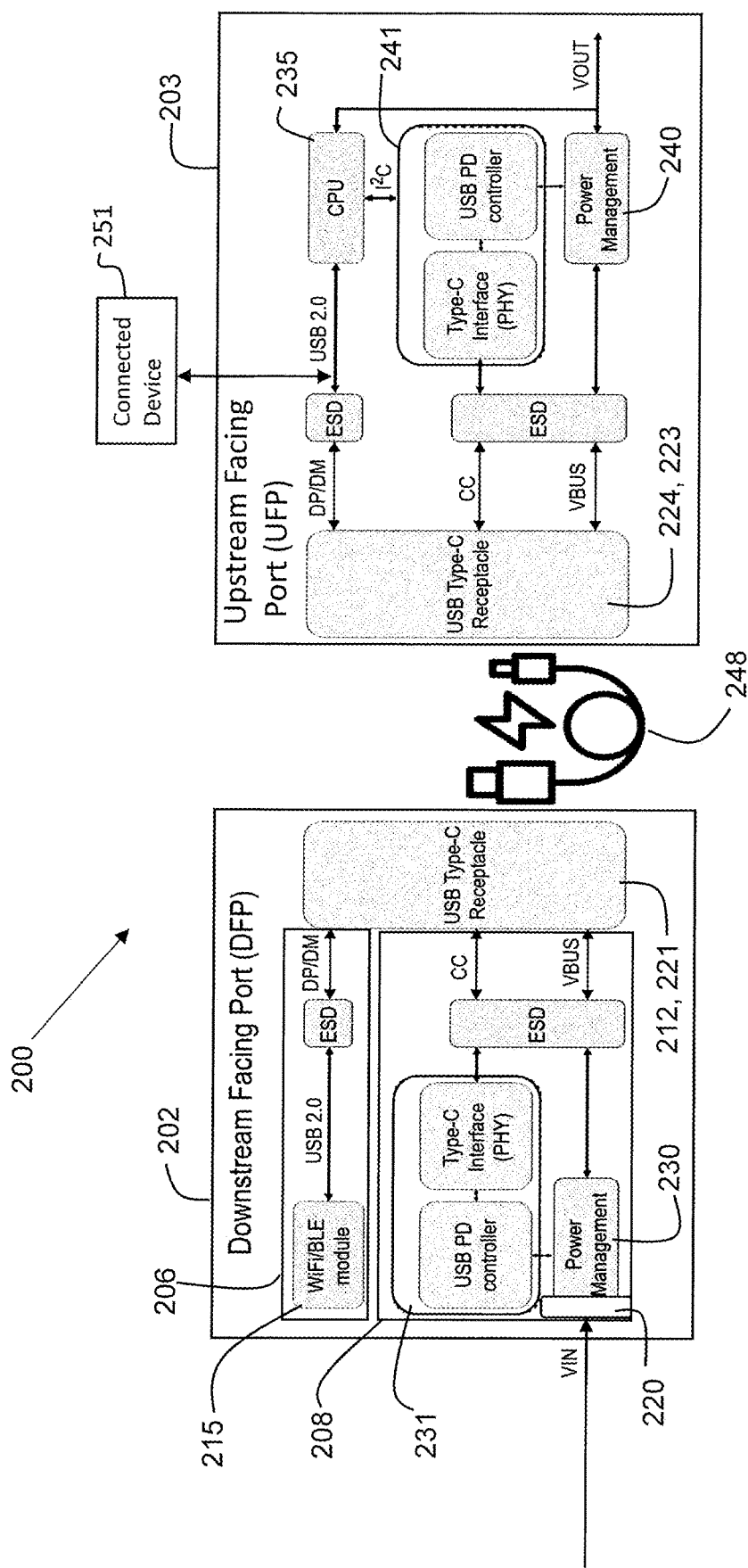
FIG. 14 schematically illustrates a sleep aid system including a smart power hub according to various embodiments described herein.

In various embodiments, the smart power hub 202 includes USB technology for one or both of power delivery or data communications. FIG. 14 illustrates a USB implementation utilizing USB type-C.

The smart power hub 203 includes a data communication system 206 and power system 208. The power system 208 includes a power port 220 for receiving a supply of power. The power supplied may be managed by a power management unit 230. Power supplied from the power management unit 230 may be supplied to a power control unit 231. The power control unit 231 may include a USB power delivery (PD) controller configured to communicate over type-C configuration channel (CC) pins to negotiate a given amount of power to be sourced to an inquiring device. The power control unit 231 may also include a type-C Interface (PHY). The power management unit 230 and power control unit 231 may include functionalities described above with respect power controller 209 (FIG. 12). Power routing may further include an electrostatic discharge unit positioned between an USB interface receptacle, comprising dual power and data communication ports 212, 221, and the power management unit 230 and the power control unit 231 along communication channel (CC) and VBUS lines. In some embodiments, the power control unit may be a STUSB4710 family USB power delivery controller, which may be configured to handle connections to an upstream facing port (UFP) without MCU attachment support from device attachment to power negotiation, including VBUS discharge and protections. The data communication system 206 includes a network module 215 for providing wireless communication as described herein. The network module 215 is shown as including WiFi and BLE technology functions. In other embodiments, other wireless protocols and/or technologies may be used. The illustrated data communication system includes USB 2.0 data transfer speeds. However, in other embodiments, higher data rates may be used. For example, SuperSpeed USB 3.0 (5 Gbps), SuperSpeed+USB 3.1 (10 Gbps), or higher may be used. An electrostatic discharge unit may be provided between the network module 215 and the power and data communication ports 212, 221 along the data transfer line, comprising a downstream facing port (DFP) with respect to the sleep aid device 203.

In the illustrated embodiment, the dual power and data communication ports 212, 221 include a USB type-C receptacle. A USB type-C connection may be made between the smart power hub 202 receptacle and the sleep aid device 203 receptacle using a wired cable connection 248. The cable is preferably 2 meters long or greater to reduce exposure electromagnetic radiation within the sleep aid device 203 from the wireless network module 215. However, shorter lengths may be used. In some embodiments, directional beaming technology or shielding with respect to the smart power hub 202 or sleep aid device 203 may be used to reduce exposure within the sleep aid device 203. In some embodiments, the cable may include power and data cables that are separated along all or a portion of the cable length. In one embodiment, the cable caries both data and power as a bundle.

The sleep aid device 203 includes a receptacle comprising dual power and data delivery ports 224, 223 comprising an upstream facing port (UFP) with respect to the smart power hub 202. Data may be transmitted between the receptacle and a CPU 235. Power may be transmitted between the receptacle, a power management unit 240, and a power controller 241. The power management unit 240, power control unit 241, and CPU 235 may be configured to process, control, or execute in whole or in part, one or more operations described above with respect to the control functionalities with respect to control systems 216, 120 (see, e.g., FIGS. 3, 12). Power routing may further include an electrostatic discharge unit positioned between the USB interface receptacle and the power management unit 240 and power control unit 241 along communication channel (CC) and VBUS lines. Data transfer line between the receptacle and the CPU 235 may include an electrostatic discharge unit.

In the illustrated embodiment, data is transferred at USB 2.0 transfer speeds. However, in other embodiments, higher data rates may be used. For example, SuperSpeed USB 3.0 (5 Gbps), SuperSpeed+USB 3.1 (10 Gbps), or higher may be used. CPU 235 may interface with the power control unit 241, e.g., at an $I^2C$ interface, to provide power-sharing applications. In some embodiments, the power control unit 241 may include a STUSB1602 USB type-C controller IC.

In one embodiment, the control system 241 is configured to remotely turn power off or on for the data communication system 206 or wireless subsystem thereof, or other components, in the smart power hub 202 by sending a USB type-C PD, or other command to the power controller 231 to change the power or current profile, which may control the power distribution system in the smart power hub 202. Such command may be used to turn off WiFi or cycle power to restart the data communication system 206 or wireless subsystem thereof, remotely by the sleep aid device 203.

In one example of the sleep aid system 200, the smart power hub 202 includes a USB power delivery controller, a type-C attachment and type-C cable orientation detection, single role provider downstream facing port (DFP), that supports all USB PD profiles up to 5 power data objects (PDO) from 5V to 20V. The sleep aid device 203 may include a USB type-C controller including, type-C cable attachment and cable orientation detection, a power role including a sink/dual role, configurable start-up profiles via $I^2C$, and may configure USB PD provider to supply various power data objects (PDO).

According to various embodiments, the smart power hub 202 provides power and wireless functions (e.g., WiFi and BLE) to the sleep aid device 203 in the form factor of a power brick. The smart power hub 202 may include a single cable for power and data transmission. The smart power hub 202 may provide desirable wireless communication functions while having wireless transmitters movable away from an infant within the sleep aid device 203.

USB type-C may be utilized as a solution that proves low latency data transfer as well as up to 100 W of electrical power. Data rates at or above USB 2.0 High Speed may be utilized. Lower data rates may be used in some embodiments but may limit performance of some applications. The network module 215 may be used to transfer device or infant status, e.g., via a WiFi connection. In some embodiments, the network module 215 may support continuous transmission of video and streaming audio. In one embodiment, local, personal, ad hoc, or similar network, such as a Bluetooth/BLE connectivity technology may be utilized for in-app authentication and WiFi configuration, e.g., passing credentials. In some embodiments, such connectivity may be utilized to control a peripheral such as a BLE peripheral. Peripherals may include, for example, a camera, microphone, display, mobile, lights, or the like. In other embodiments, the smart power hub 202 may include other configurations of USB type C and/or other USB technologies such as USB 2.0, 3.0, or 3.1.

In some examples, the smart power hub 202 or network module 215 thereof may be configured for near field communications. For example, the network module 215 may have a NFC transmitter/receiver/transceiver that can pair with and communicate with a corresponding NFC transmitter/receiver/transceiver included in the user interface (e.g., a Smartphone or tablet computer). The user interface and network module 215 may communicate using a protocol that requires very close proximity between the two devices (e.g., a distance of a few inches or a few feet).

While the smart power hub 202 is generally described herein for operation with an sleep aid device 203, those having skill in the art will appreciate that the smart power hub may be used with other sleep aid devices such as powered beds for children, adolescences, adults, seniors, or disabled or sick individuals. For example, the smart power hub 202 may be configured for operation with an infant monitor or hospital bed. In some embodiments, the smart power hub does not provide power. Embodiments of the smart power hub 202 may be configured for use with any electronic device. The electronic device may be a device that is configured for operation proximate to an individual. For example, in one embodiment, the smart power hub 202 is configured for operation with an electronic device configured for operation proximate to an individual. For example, the operation distance may be 5 meters or less, such as about 4 meters or less, about 3 meters or less, about 2 meters or less, or about 1 meter or less. The smart power hub 202 may provide wireless communication functions and power functions or may provide wireless communication functions without providing power functions for the electronic device. The electronic device may be an infant or child monitor configured to monitor sound, movement, location, or breathing, as examples. The electronic device may be configured for operation proximate to an infant or child, e.g., worn on the infant or child as clothing, wrap, bracelet. In one embodiment, the electronic device is a wireless phone configured for operation proximate to a child or adult. The smart power hub 202 may be configured to couple to the wireless phone via a wired connection whereby the smart power hub being spaced away from the electronic device may provide wireless communication as described herein a safe distance away from the individual using the wireless phone. The smart power hub 202 may also provide network services for connected devices 251 that may be connected to the sleep aid device 203. Such a connected device 215 may be connected to the sleep aid device 203 via USB, wireless, or other connection technologies. Suitable connections or interfaces may be provided by the sleep aid device 203 for achieving such connections. Providing such network services allows utilization of connected devices 251 that may not include network hardware capabilities. Such a connected device 251 could be a camera, lights, music player, etc.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" refers to "x", "y", or both "x" and "y", whereas "either x or y" refers to exclusivity.

This disclosure describes various elements, features, aspects, and advantages of various embodiments, configurations, and arrangements of the oven systems, apparatuses, and methods thereof. It is to be understood that certain descriptions of the various embodiments and such configurations and arrangements thereof have been simplified to illustrate only those elements, features and aspects that are relevant to a more clear understanding of the disclosed embodiments, while eliminating, for purposes of brevity or clarity, other elements, features and aspects. Any references to "various," "certain," "some," "one," or "an" when followed by "embodiment," "configuration," or "arrangement" generally means that a particular element, feature or aspect described in the example is included in at least one embodiment. The phrases "in various," "in certain," "in some," "in one," or "in an" when followed by "embodiment", "configuration", or "arrangement" may not necessarily refer to the same embodiment. Furthermore, the phrases "in one such" or "in this" when followed by "embodiment," "configuration," or "arrangement," while generally referring to and elaborating upon a preceding embodiment, is not intended to suggest that the elements, features, and aspects of the embodiment introduced by the phrase are limited to the preceding embodiment; rather, the phrase is provided to assist the reader in understanding the various elements, features, and aspects disclosed herein and it is to be understood that those having ordinary skill in the art will recognize that such elements, features, and aspects presented in the introduced embodiment may be applied in combination with other various combinations and sub-combinations of the elements, features, and aspects presented in the disclosed embodiments. It is to be appreciated that persons having ordinary skill in the art, upon considering the descriptions herein, will recognize that various combinations or sub-combinations of the various embodiments and other elements, features, and aspects may be desirable in particular implementations or applications. However, because such other elements, features, and aspects may be readily ascertained by persons having ordinary skill in the art upon considering the description herein, and are not necessary for a complete understanding of the disclosed embodiments, a description of such elements, features, and aspects may not be provided. For example, ovens and oven systems described herein may also include connections such as fittings for one or more of electrical connections, gas connections, or flue connections. As such, it is to be understood that the description set forth herein is merely exemplary and illustrative of the disclosed embodiments and is not intended to limit the scope of the invention as defined solely by the claims.

What is claimed is:

1. A smart power hub for a sleep aid device, the smart power hub comprising:
   a power system configured to transmit a supply of power to the sleep aid device; and
   a data communication system configured to transmit and receive data between the sleep aid device and a user communication device or network,
   wherein the data communication system is configured to receive media data from the user communication device or network and transmit the media data to the sleep aid device for presentation of the media data from at least one of a speaker or a display associated with the sleep aid device, and
   wherein the data communication system is configured to store the media data and then transmit the media data to the sleep aid device for the presentation upon occurrence of an event.

2. The smart power hub of claim 1, wherein the data communication system includes a network module configured to provide wireless communication services for data communications between the sleep aid device and the user communication device or network.

3. The smart power hub of claim 2, wherein the smart power hub transmits and receives data communications to and from the sleep aid device via a wired connection and transmits and receives data communications to the user communication device or network via wireless communication utilizing the network module.

4. The smart power hub of claim 3, wherein the wired connection comprises a cable having a length of at least 2 meters, and wherein the cable transmits both power from the power system and data communications from the data communication system.

5. The smart power hub of claim 2, wherein the network module communicates within a wireless personal area network protocol to provide the user communication device, that is in wireless communication with the network module via a wireless personal area network, control of operations of the sleep aid device.

6. The smart power hub of claim 5, wherein the wireless personal area network protocol is carried over a short-wavelength UHF radio wave communication wireless network technology comprising a low energy wireless personal area network technology.

7. The smart power hub of claim 2, wherein the network module is configured with wireless networking capabilities using both WiFi and short-wavelength UHF radio wave communication technologies.

8. The smart power hub of claim 2, wherein the smart power hub supports transmission of continuous 1080p video and continuous streaming audio.

9. The smart power hub of claim 2, wherein the smart power hub provides an internet access point and is configured to receive software updates via internet communications to update the smart power hub, to update the sleep aid device, or both.

10. The smart power hub of claim 2, wherein the smart power hub provides an internet access point to the user communication device running an application configured to communicate with the sleep aid device when the user communication device is authenticated.

11. The smart power hub of claim 10, wherein the network module provides short-wavelength UHF radio wave communication support for in-application authentication.

12. The smart power hub of claim 2, wherein the network module provides short-wavelength UHF radio wave communication technology support for:
WiFi configuration,
WiFi configuration comprising passing credentials,
controlling a low energy short-wavelength UHF radio wave communication technology peripheral, or
a combination thereof.

13. The smart power hub of claim 2, wherein the smart power hub is configured to transmit power and data communications to the sleep aid device using a single cable, coupled directly or via an intermediate cable to a wall outlet, and convert alternating current to direct current.

14. A sleep aid system, the system comprising:
a sleep aid device comprising:
a platform,
a motor to move the platform,
one or more sensors for monitoring an infant when positioned on the platform, and
a control system operable to control operation of the motor to thereby control a movement of the platform, wherein the control system is configured to receive infant data collected by the one or more sensors with respect to the infant when positioned on the platform, and wherein the control system is configured to modify the movement of the platform based on analysis of the infant data;
at least one of a speaker or a display; and
a smart power hub comprising:
a power system configured to transmit a supply of power to the sleep aid device; and
a data communication system configured to transmit and receive data between the sleep aid device and a user communication device or network,
wherein the data communication system is configured to receive media data from the user communication device or network and transmits the media data to the sleep aid device, and wherein the sleep aid device is configured to present the media data with at least one of the at least one speaker or display.

15. The system of claim 14, wherein the sleep aid device is configured to present the media data upon a determination of a status of the infant based on analysis of the infant data.

16. A smart power hub for a sleep aid device, the smart power hub comprising:
a power system configured to transmit a supply of power to the sleep aid device; and
a data communication system configured to transmit and receive data between the sleep aid device and a user communication device or network,
wherein the data communication system is configured to receive media data from the user communication device or network and transmit the media data to the sleep aid device for presentation of the media data from at least one of a speaker or a display associated with the sleep aid device, and
wherein the data communication system is configured to store the media data and then transmit the media data to the sleep aid device for the presentation at a set time.

* * * * *